US 7,856,707 B2

(12) United States Patent
Cole

(10) Patent No.: US 7,856,707 B2
(45) Date of Patent: Dec. 28, 2010

(54) METHOD FOR PERFORMING A COPLANAR CONNECTION BETWEEN A CONDUCTOR AND A CONTACT ON AN IMPLANTABLE LEAD

(75) Inventor: Mary Lee Cole, St. Paul, MN (US)

(73) Assignee: Medtronic, Inc., Minneapolis, MN (US)

( * ) Notice: Subject to any disclaimer, the term of this patent is extended or adjusted under 35 U.S.C. 154(b) by 720 days.

(21) Appl. No.: 10/412,014

(22) Filed: Apr. 11, 2003

(65) Prior Publication Data

US 2004/0019372 A1    Jan. 29, 2004

Related U.S. Application Data

(63) Continuation-in-part of application No. 10/131,106, filed on Apr. 22, 2002.

(51) Int. Cl.
*H01R 9/00* (2006.01)
*H05K 3/00* (2006.01)

(52) U.S. Cl. .............................. 29/844; 29/825; 29/861; 607/116; 607/117; 607/132

(58) Field of Classification Search ................... 29/844, 29/825, 861, 746; 607/101, 116, 117, 119, 607/122, 132; 156/143, 196; 600/372; 609/101, 609/116, 117, 119, 122, 132
See application file for complete search history.

(56) References Cited

U.S. PATENT DOCUMENTS

| | | | |
|---|---|---|---|
| 1,674,804 A | 6/1928 | Stearns | |
| 3,289,149 A | 11/1966 | Pawloski | |
| 3,565,074 A | 2/1971 | Foti | |
| 3,819,418 A * | 6/1974 | Winkler et al. | ............... 136/205 |
| 4,161,952 A * | 7/1979 | Kinney et al. | ................ 607/122 |
| 4,207,900 A | 6/1980 | Patel et al. | |
| 4,280,511 A | 7/1981 | O'Neill | ....................... 128/784 |
| 4,325,599 A | 4/1982 | Feldman | |
| 4,328,812 A | 5/1982 | Ufford et al. | |
| 4,335,930 A | 6/1982 | Feldman | |

(Continued)

FOREIGN PATENT DOCUMENTS

DE           3300723           7/1984

(Continued)

*Primary Examiner*—Thiem Phan
(74) *Attorney, Agent, or Firm*—Fredrikson & Byron, P.A.

(57) ABSTRACT

An implantable lead for a medical device with a coplanar coupling for connecting a conductor to a contact reduces conductor bending moments to improve lead reliability. The implantable lead comprises a lead body having a proximal end and a distal end, at least one conductor, at least one contact carried on the proximal end, at least one contact carried on the distal end, and at least one coupling. The lead body has an exterior surface. The conductor is contained in the lead body and extends from the lead proximal end to the distal end. The conductor is also electrically insulated. The contact carried on the proximal end is electrically connected to the conductor. The coupling has a conductor coupling and a contact coupling. The conductor coupling is placed over the conductor and attached to the conductor. The contact coupling exits the lead body and has a weld to connect the contact coupling to the contact. The contact coupling is configured to exit the conductor lumen and mate with the contact while retaining the conductor coplanar to the lead body.

8 Claims, 23 Drawing Sheets

U.S. PATENT DOCUMENTS

| | | | |
|---|---|---|---|
| 4,413,636 A | 11/1983 | Jasso | |
| 4,499,907 A | 2/1985 | Kallok et al. | |
| 4,522,212 A | 6/1985 | Gelinas et al. | |
| 4,633,889 A | 1/1987 | Talalla et al. | |
| 4,777,955 A | 10/1988 | Brayton et al. | |
| 4,835,853 A | 6/1989 | Hirschberg | |
| 4,920,980 A | 5/1990 | Jackowski | |
| 4,955,382 A | 9/1990 | Franz et al. | |
| 5,007,888 A * | 4/1991 | Goutiere | 439/189 |
| 5,014,696 A | 5/1991 | Mehra | |
| 5,016,646 A | 5/1991 | Gotthardt et al. | 128/784 |
| 5,115,818 A | 5/1992 | Holleman et al. | |
| 5,265,623 A | 11/1993 | Kroll et al. | |
| 5,370,675 A | 12/1994 | Edwards et al. | |
| 5,385,544 A | 1/1995 | Edwards et al. | |
| 5,385,578 A | 1/1995 | Bush et al. | |
| 5,409,453 A | 4/1995 | Lundquist et al. | |
| 5,421,819 A | 6/1995 | Edwards et al. | |
| 5,435,805 A | 7/1995 | Edwards et al. | |
| 5,454,787 A | 10/1995 | Lundquist | |
| 5,458,629 A | 10/1995 | Baudino et al. | |
| 5,488,768 A | 2/1996 | Mar | |
| 5,525,070 A * | 6/1996 | Axelsson | 439/268 |
| 5,531,677 A | 7/1996 | Lundquist et al. | |
| 5,549,644 A | 8/1996 | Lundquist et al. | |
| 5,562,722 A | 10/1996 | Racz et al. | |
| 5,569,883 A | 10/1996 | Walter et al. | |
| 5,578,067 A | 11/1996 | Ekwall et al. | |
| 5,584,873 A | 12/1996 | Shoberg et al. | |
| 5,628,774 A | 5/1997 | Helland et al. | |
| 5,667,488 A | 9/1997 | Lundquist et al. | |
| 5,673,704 A | 10/1997 | Marchlinski et al. | |
| 5,674,273 A | 10/1997 | Helland | |
| 5,676,694 A | 10/1997 | Boser et al. | |
| 5,685,868 A | 11/1997 | Lundquist | |
| 5,720,719 A | 2/1998 | Edwards et al. | |
| 5,762,626 A | 6/1998 | Lundquist et al. | |
| 5,807,309 A | 9/1998 | Lundquist et al. | |
| 5,848,986 A | 12/1998 | Lundquist et al. | |
| 5,869,804 A | 2/1999 | Mueller et al. | |
| 5,935,159 A | 8/1999 | Cross, Jr. et al. | |
| 6,016,436 A | 1/2000 | Bischoff et al. | |
| 6,052,625 A | 4/2000 | Marshall | |
| 6,102,886 A | 8/2000 | Lundquist et al. | |
| 6,161,047 A | 12/2000 | King et al. | |
| 6,181,971 B1 | 1/2001 | Doan | |
| 6,216,045 B1 | 4/2001 | Black et al. | |
| 6,241,702 B1 | 6/2001 | Lundquist et al. | |
| 6,249,709 B1 | 6/2001 | Conger et al. | |
| 6,256,542 B1 | 7/2001 | Marshall et al. | |
| 6,285,910 B1 * | 9/2001 | Verness et al. | 607/122 |
| 6,289,251 B1 | 9/2001 | Huepenbecker et al. | |
| 6,292,702 B1 | 9/2001 | King et al. | |
| 6,319,241 B1 | 11/2001 | King et al. | |
| 6,366,820 B1 | 4/2002 | Doan et al. | |
| 6,381,835 B1 | 5/2002 | Conger et al. | |
| 6,400,992 B1 | 6/2002 | Borgersen et al. | |
| 6,415,187 B1 | 7/2002 | Kuzma et al. | |
| 6,442,435 B2 | 8/2002 | King et al. | |
| 6,522,932 B1 | 2/2003 | Kuzma et al. | |
| 6,606,521 B2 * | 8/2003 | Paspa et al. | 607/116 |
| 6,714,822 B2 | 3/2004 | King et al. | |
| 6,792,317 B1 | 9/2004 | Doan et al. | 607/122 |
| 6,795,737 B2 | 9/2004 | Gielen et al. | |
| 6,981,314 B2 | 1/2006 | Black et al. | |
| 7,184,840 B2 | 2/2007 | Stolz | |
| 7,343,206 B2 | 3/2008 | Sage et al. | |
| 2001/0018607 A1 | 8/2001 | Borgersen et al. | |
| 2001/0023367 A1 | 9/2001 | King et al. | |
| 2001/0023368 A1 | 9/2001 | Black et al. | |
| 2001/0053885 A1 | 12/2001 | Gielen et al. | |
| 2002/0055765 A1 | 5/2002 | Black et al. | |
| 2002/0151948 A1 | 10/2002 | King et al. | |
| 2002/0183824 A1 | 12/2002 | Borgersen et al. | |
| 2002/0193860 A1 | 12/2002 | Bischoff et al. | |
| 2003/0199952 A1 | 10/2003 | Stolz et al. | |
| 2003/0199953 A1 | 10/2003 | Stoltz et al. | |
| 2004/0024440 A1 | 2/2004 | Cole | |
| 2004/0186543 A1 | 9/2004 | King et al. | |
| 2004/0236388 A1 | 11/2004 | Gielen et al. | |
| 2005/0138791 A1 | 6/2005 | Black et al. | |
| 2005/0138792 A1 | 6/2005 | Black et al. | |
| 2006/0155343 A1 | 7/2006 | Vilims | |
| 2006/0229693 A1 | 10/2006 | Bauer et al. | |
| 2006/0259106 A1 | 11/2006 | Arnholt et al. | |
| 2007/0168007 A1 | 7/2007 | Kuzma et al. | |
| 2007/0213795 A1 | 9/2007 | Bradley et al. | |
| 2007/0213796 A1 | 9/2007 | McGinnis | |

FOREIGN PATENT DOCUMENTS

| | | |
|---|---|---|
| EP | 0506620 | 9/1992 |
| EP | 1048317 | 11/2000 |
| SE | 70446 | 9/1927 |
| WO | WO9417856 | 8/1994 |
| WO | WO9505124 | 2/1995 |
| WO | WO97/09012 | 3/1997 |
| WO | WO99/53994 | 10/1999 |
| WO | WO99/55411 | 11/1999 |
| WO | WO0027469 | 5/2000 |
| WO | WO0048665 | 8/2000 |
| WO | WO0054833 | 9/2000 |
| WO | WO00/64530 | 11/2000 |

\* cited by examiner

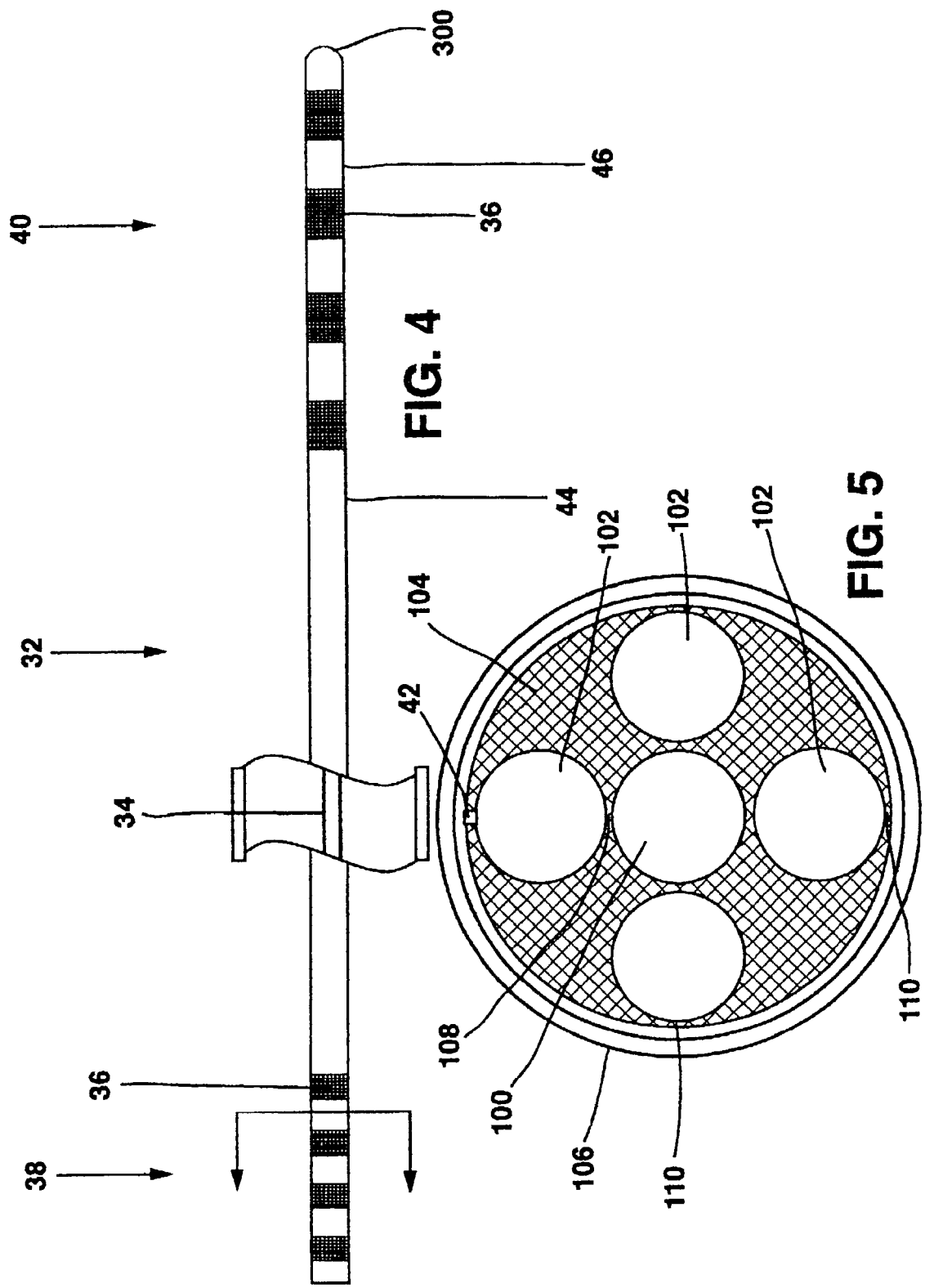

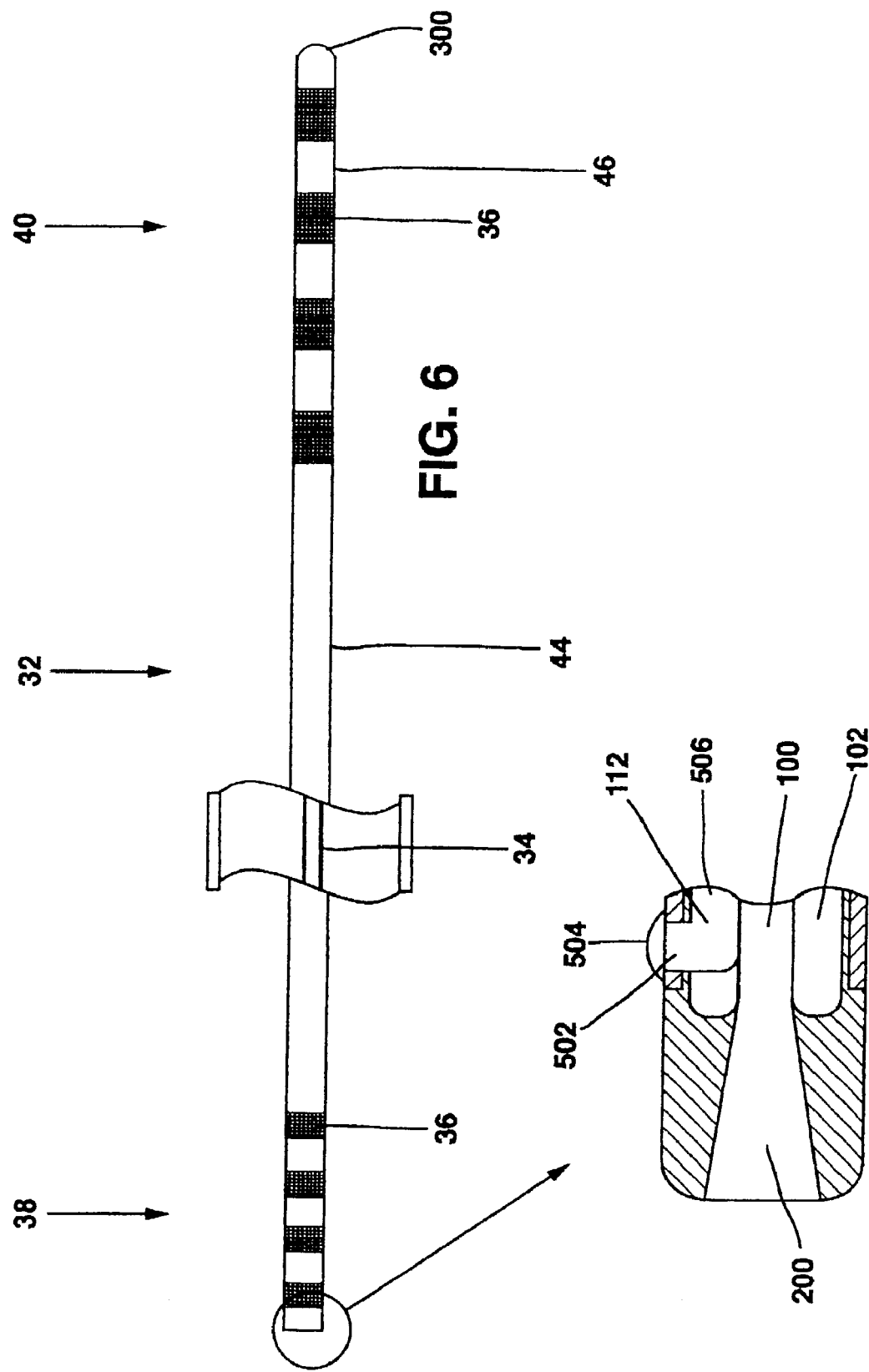

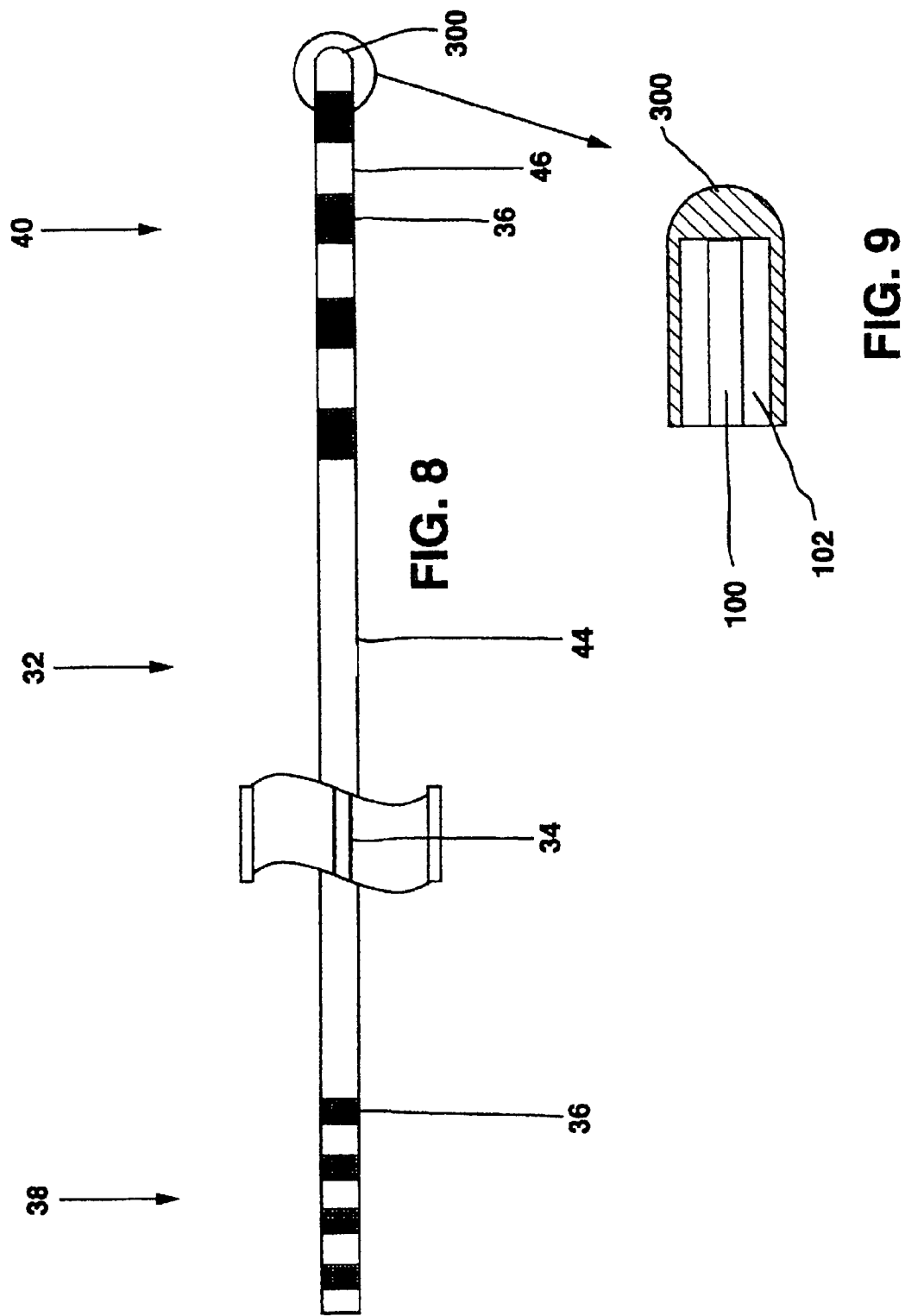

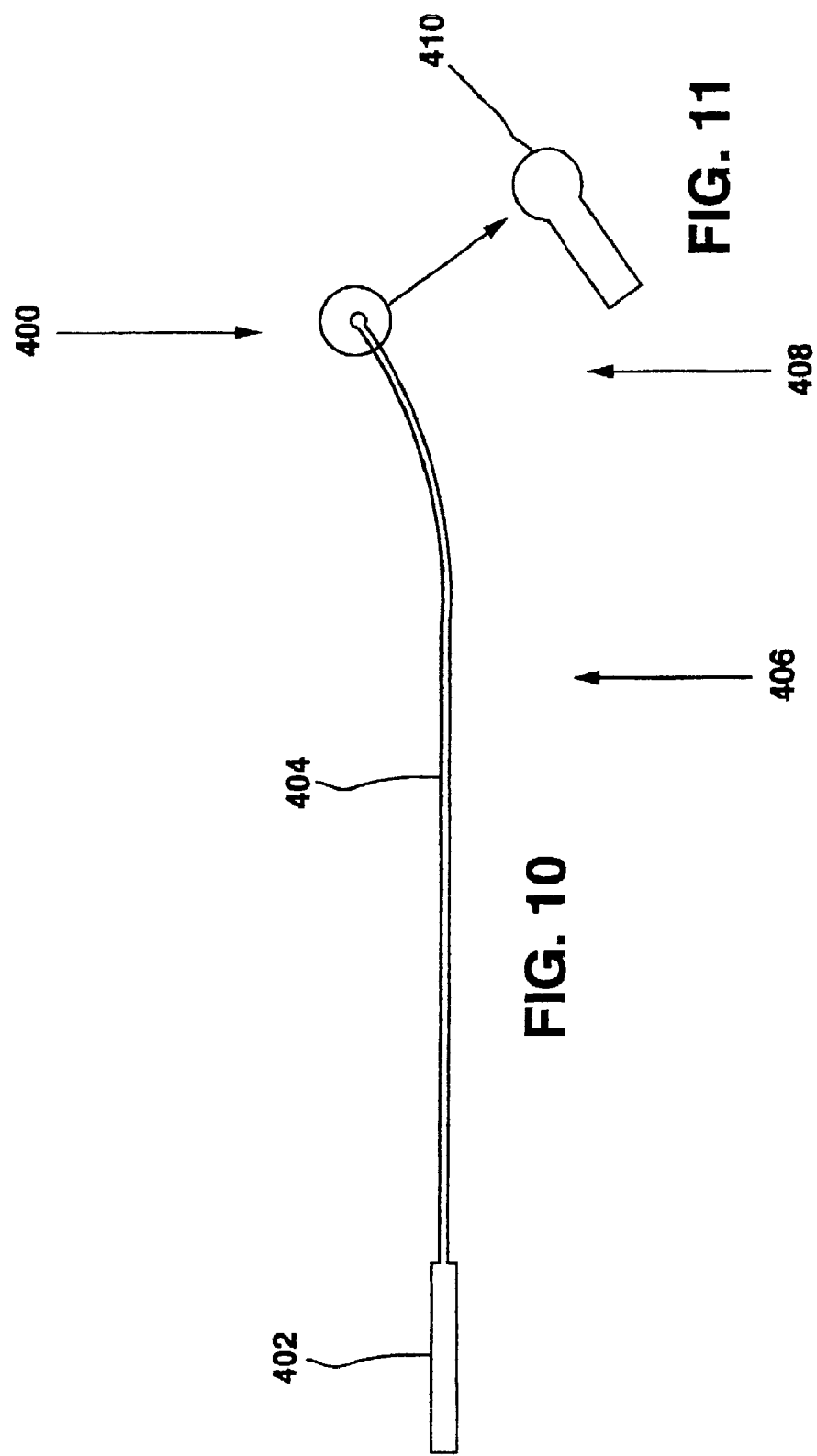

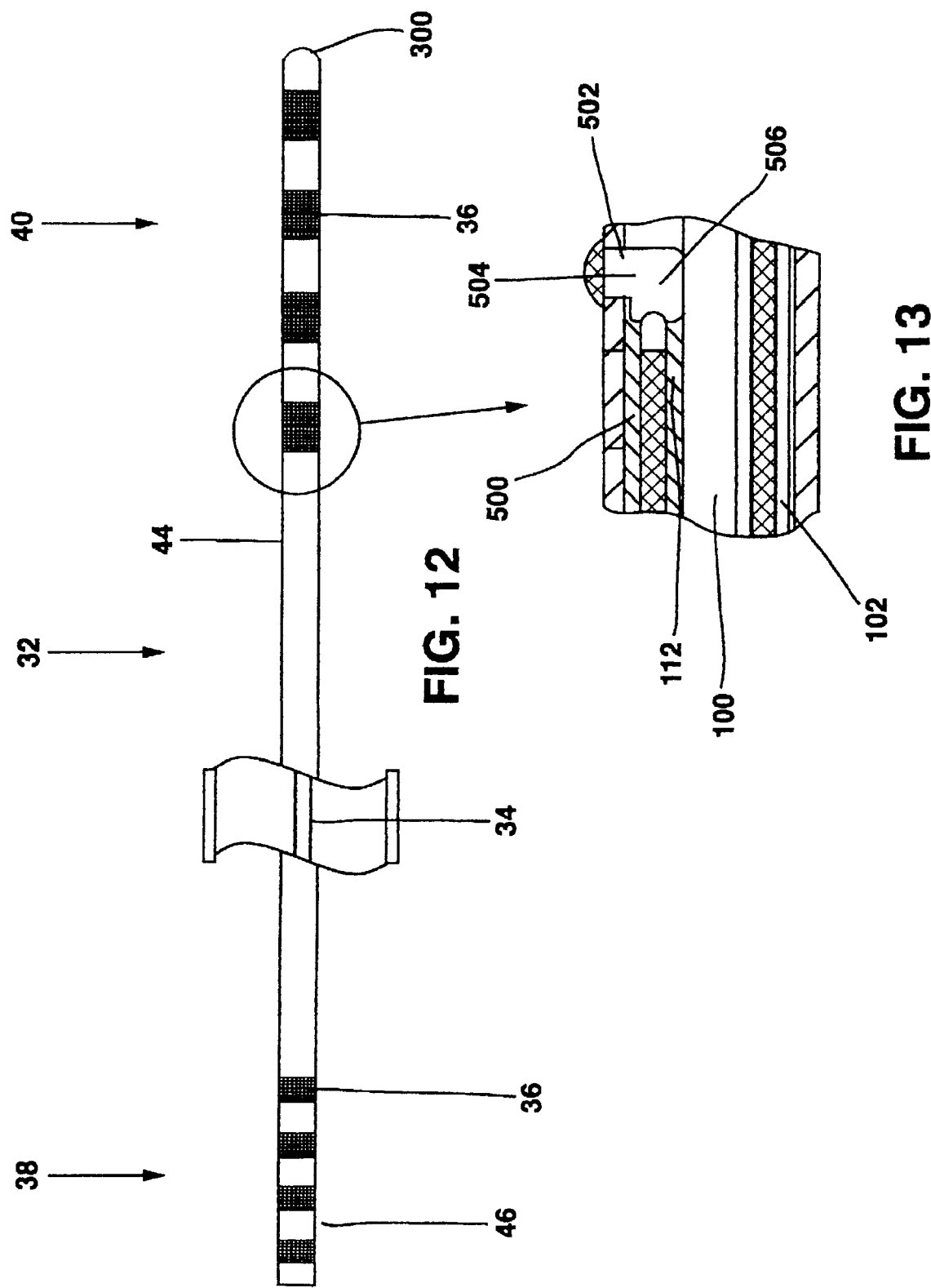

METHOD FOR PERFORMING A COPLANAR CONNECTION BETWEEN A CONDUCTOR AND A CONTACT ON AN IMPLANTABLE LEAD

CROSS REFERENCES

This application is a continuation in part of application Ser. No. 10/131,106, to Pardo et. al. filed Apr. 22, 2002.

BACKGROUND OF THE INVENTION

This disclosure relates to medical devices and more particularly to an implantable lead.

The medical device industry produces a wide variety of electronic and mechanical devices for treating patient medical conditions such as pacemakers, defibrillators, neurostimulators and therapeutic substance delivery pumps. Medical devices can be configured to be surgically implanted or connected externally to the patient receiving treatment. Clinicians use medical devices alone or in combination with therapeutic substance therapies and surgery to treat patient medical conditions. For some medical conditions, medical devices provide the best and sometimes the only therapy to restore an individual to a more healthful condition and a fuller life. One type of medical device is an implantable neurological stimulation system that can be used to treat conditions such as pain, movement disorders, pelvic floor disorders, gastroparesis, and a wide variety of other medical conditions. The neurostimulation system typically includes a neurostimulator, a stimulation lead, and an extension such as shown in Medtronic, Inc. brochure "Implantable Neurostimulation System" (1998). More specifically, the neurostimulator system can be an Itrel II® Model 7424 or an Itrel 3® Model 7425 available from Medtronic, Inc. in Minneapolis, Minn. that can be used to treat conditions such as pain, movement disorders and pelvic floor disorders. The neurostimulator is typically connected to a stimulation lead that has one or more electrodes to deliver electrical stimulation to a specific location in the patient's body.

Implantable leads have conductors that are connected to contacts to form electrical path. The connection between the conductors and the contacts should have solid mechanical connection and a low impedance electrical connection for efficient operation and reliability. Conductors manufactured from low impedance materials such as silver make forming a connection with good mechanical properties challenging because silver has substantially less tensile strength than a more common conductor material such as MP35N. Additionally, silver content in the weld joint between a conductor and contact increases the chances of separation, silver exposure to tissue, and weld corrosion during lead operation. Conductor bending moments should be avoided at the connection because bending moments can stress the conductor and reduce the reliability of the connection. Previous conductor to contact lead connections involve creating a bending moment in the conductor at or near the connection. An example of a lead with a joined conductor and electrode is shown in U.S. Pat. No. 6,181,971 "Joining Conductor Cables And Electrodes On A Multi-Lumen Lead Body" by Doan (Jan. 30, 2001).

For the foregoing reasons, there is a need for an implantable lead with coplanar contact couplings to reduce conductor bending moments to improve lead reliability.

BRIEF SUMMARY OF THE INVENTION

An implantable lead with a coplanar coupling for connecting a conductor to a contact to reduce conductor bending moments to improve lead reliability. The implantable lead comprises a lead body having a proximal end and a distal end, at least one conductor, at least one contact carried on the proximal end, at least one contact carried on the distal end, and at least one coupling. The lead body has an exterior surface. The conductor is contained in the lead body and extends from the lead proximal end to the distal end. The conductor is also electrically insulated. The contact carried on the proximal end is electrically connected to the conductor. The coupling has a conductor coupling and a contact coupling. The conductor coupling is placed over the conductor and attached to the conductor. The contact coupling exits the lead body and has a weld to connect the contact coupling to the contact. The contact coupling is configured to exit the conductor lumen and mate with the contact while retaining the conductor coplanar to the lead body.

Another aspect of the present invention provides for an implantable lead with a coplanar coupling for connecting a conductor to a contact to reduce conductor bending moments to improve lead reliability. The implantable lead comprises a lead body having a proximal end, a distal end, at least one conductor, at least one contact carried on the proximal end, at least one contact carried on the distal end, and at least one coupling. The conductor is contained within the lead body and traverses from the proximal end to the distal end of the lead body. The contact carried on the proximal end and the contact carried on the distal end are electrically connected to the conductor. The conductor coupling is partially placed over the conductor and attached to the conductor. The conductor coupling is then placed in a channel on the at least one contact and welded to connect the conductor coupling to the at least one contact. The conductor does not exit the lead body and remains substantially coplanar with the contact to prevent bending of the conductor.

Another aspect of the present invention provides for a method for performing a coplanar connection between a conductor and a contact on an implantable lead to reduce conductor bending moments and improve lead reliability. A conductor is inserted into a crimp sleeve cavity and then crimped to securely attach the conductor to the crimp sleeve. The crimp sleeve is then inserted into a channel located on the contact. The conductor is then positioned substantially coplanar with the contact body to prevent bending of the conductor. The crimp sleeve is then attached to the contact.

BRIEF DESCRIPTION OF THE DRAWINGS

FIG. 4 shows an implantable lead and features an exploded cross-section view of the conductor traversing through the lead body;

FIG. 5 shows a cross section of the implantable lead embodiment shown in FIG. 4;

FIG. 6 shows an implantable lead with proximal end enlargement indication embodiment and features an exploded cross-section view of the conductor traversing through the lead body;

FIG. 7 shows an enlarged cross section of the proximal end shown in FIG. 6;

FIG. 8 shows an implantable lead with proximal end enlargement indication embodiment and features an exploded cross-section view of the conductor traversing through the lead body;

FIG. 9 shows an enlarged cross section of the distal end shown in FIG. 8 embodiment;

FIG. 10 shows a stylet with distal end enlargement indication embodiment;

FIG. 11 shows the enlarged distal end shown in FIG. 10 embodiment;

FIG. 12 shows an implantable lead with the distal tip of the lead circled and an exploded cross-section view of the conductor traversing through the lead body;

FIG. 13 shows a cross section of the enlarged contact embodiment;

DETAILED DESCRIPTION OF THE PREFERRED EMBODIMENTS

Figure 1:
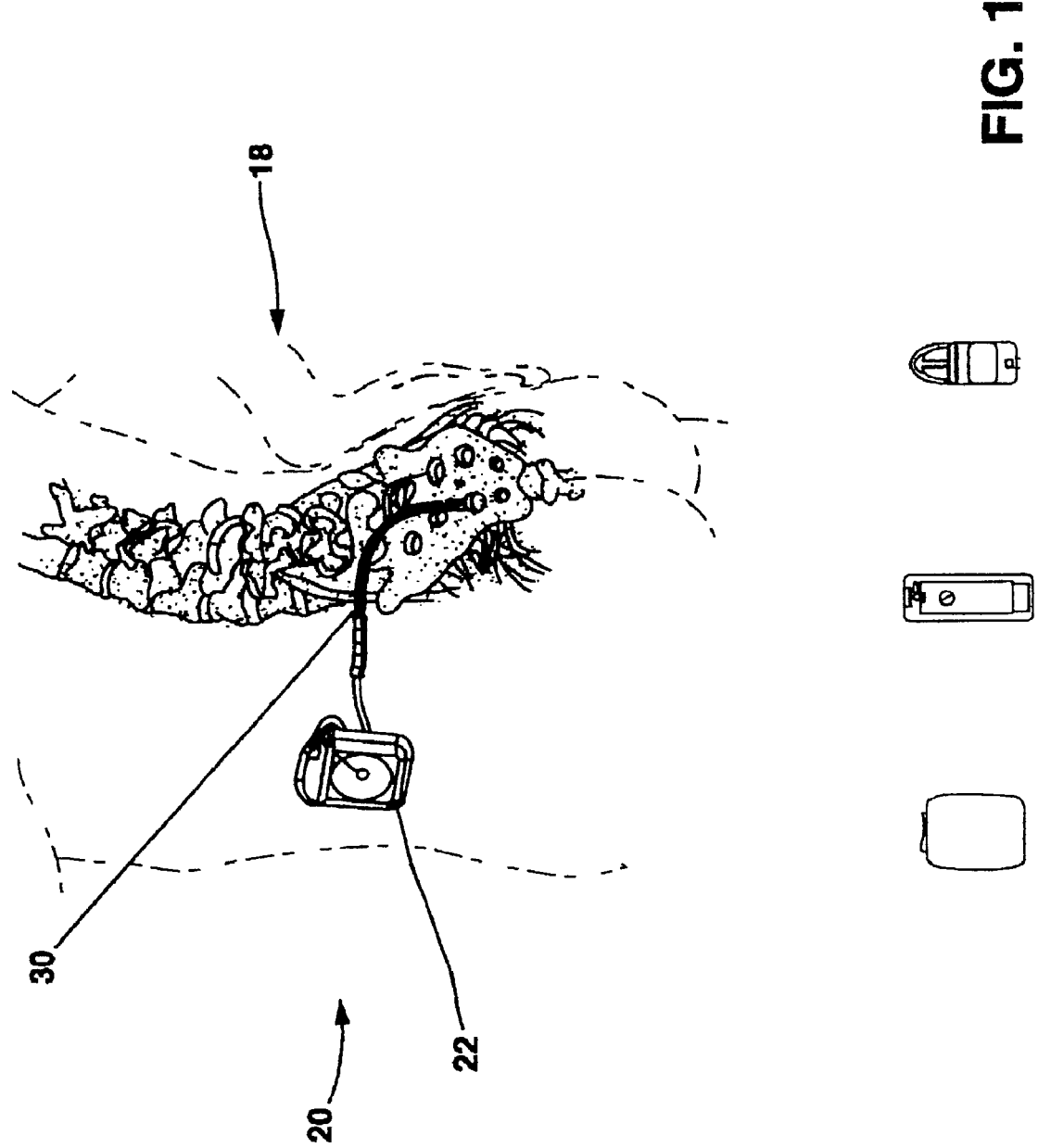
FIG. 1 shows a general environmental view for a neurostimulation system embodiment.
Figure 2:
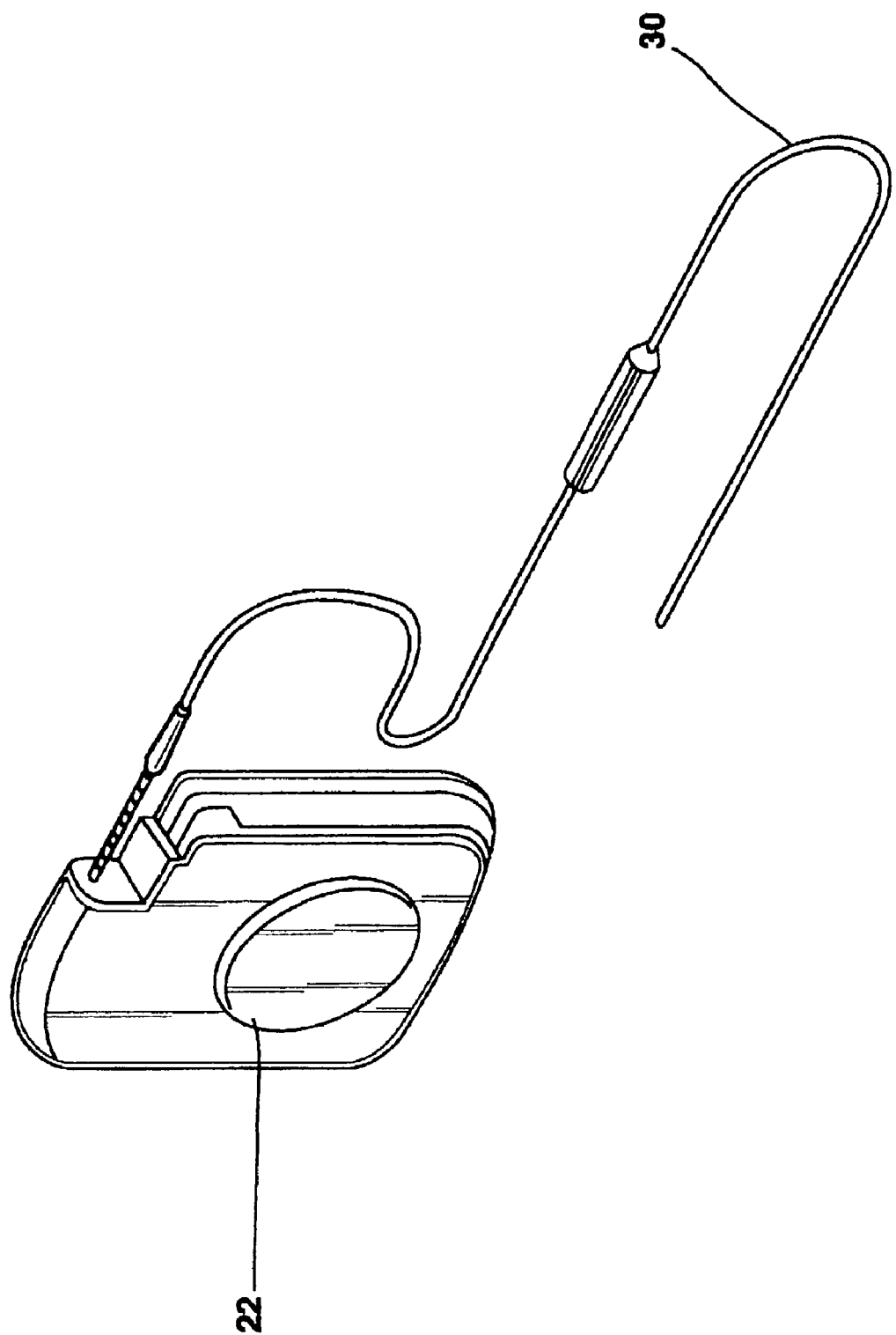
FIG. 2 shows a neurostimulation system embodiment.

FIG. 1 shows a general environmental view of an implantable neurostimulation system embodiment and FIG. 2 shows a neurostimulation system embodiment. Neurostimulation systems are used to treat conditions such as pain, movement disorders, pelvic floor disorders, gastroparesis, and a wide variety of other medical conditions. The neurostimulation system 20 includes a neurostimulator 22 such as an Itrel II® Model 7424 or an Itrel 3® Model 7425 available from Medtronic, Inc. in Minneapolis, Minn., a stimulation lead extension 24, and a stimulation lead 30. The neurostimulator 22 is typically implanted subcutaneously in the patient's body 18 at a location selected by the clinician. The stimulation lead 30 is typically fixed in place near the location selected by the clinician using a device such as the adjustable anchor. The implantable lead 30 can be configured as a neurological stimulation lead, a neurological sensing lead, and a combination of both as a neurological stimulation and sensing lead, a cardiac lead, and the like.

Figure 3:
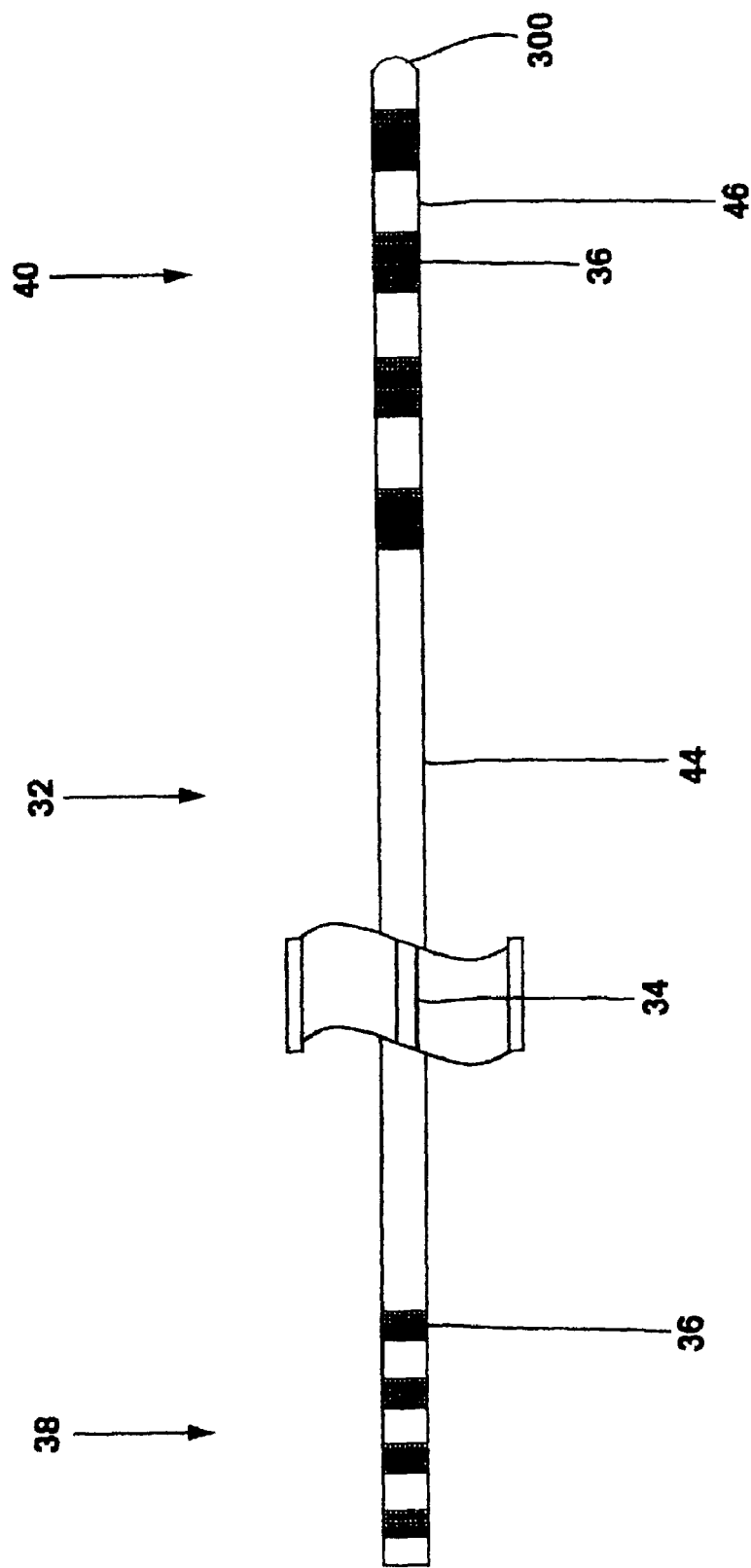
FIG. 3 shows an implantable lead embodiment and features an exploded cross-section view of the conductor traversing through the lead body.

FIG. 3 shows an implantable lead embodiment. An implantable lead comprises a lead body 32, at least one conductor 34, at least two contacts 36. The lead body has a proximal end 38, a distal end 40, and an exterior surface 44. The lead body 32 can be composed of a wide variety of electrically isolative materials and configurations. Materials may include, but are not limited to, silicone rubber, polyurethane, fluoropolymers and the like. Configurations could include monolumen and multilumen lead bodies. The exterior surface 44 is composed of one or more biocompatible materials.

The conductor 34 is contained in the lead body and generally extends from the lead proximal end 38 to the distal end 40. The conductors 34 can be manufactured from a wide range of materials that are electrically conductive such as MP35N, platinum and the like. In some embodiments, the conductor 34 can comprise a plurality of wires that can be configured as braided strand wire (BSW). BSW is available in many configurations including seven wire BSW. When low impedance is desired, the core of each wire can be manufactured from a low impedance metal such as silver and the jacket can be manufactured from a material with good mechanical strength properties such as MP35N. One embodiment of conductor 34 uses seven wire BSW with a silver core and an MP35N jacket typically with a resistance of less than about 0.098 ohms/cm (3 ohms/foot) and a tensile strength greater than 5N. The conductor 34 can be electrically insulated with a flouro-polymer such as ethyletetraflouroethylene with a coating thickness of approximately 0.002 cm (0.0008 inch).

The contacts 36 includes at least one contact 36 carried on the lead distal end 40 that is electrically connected to the conductor 34 and at least one contact 36 carried on the proximal end 38 that is electrically connected to the conductor 34. The proximal contacts are typically manufactured from a material with good mechanical strength and biocompatible properties such as MP35N and the like to withstand interaction with mating devices such as an implantable neurological extension. The distal contacts are typically manufactured from materials with good electrical and biocompatibility properties such as platinum and iridium alloys that can be configured in a mixture such as 90% platinum and 10% iridium. In some embodiments, spacers 46 are inserted between contacts 36 so the proximal end 38 and distal end 40 are substantially iso-diametric.

FIG. 4 shows an implantable lead embodiment, and FIG. 5 shows a cross section of the implantable lead in FIG. 4. An implantable lead with improved conductor lumens comprises a lead body 32, a stylet lumen 100, at least one conductor lumen 102, and at least one axial slit 42. The lead body has an internal portion 104 and an external portion 106. The stylet lumen 100 and the conductor lumen 102 are formed in the internal portion 104. The internal portion 104 is a continuous material that has a proximal end 38, distal end 40 and an outer surface that is encapsulated by the external portion 104. This structure can be extruded and its configuration can be substantially the same at any longitudinal cross section. The internal portion 104 has an outside diameter smaller than the inside diameter of the external portion 106. In some embodiments, the internal portion 104 outside diameter is approximately 0.102 cm (0.04 inch) smaller than the external portion 104 inside diameter. The internal portion 104 is fitted inside of the external portion 106. The external portion 106 exterior surface 44 typically has an outer diameter selected for the therapeutic application such as in the range from about 0.05 cm (0.02 inch) to about 0.20 cm (0.08 inch) with one embodiment having an outer diameter of about 0.127 cm (0.05 inch). The stylet lumen 100 is formed in the internal portion 104 typically in the center and sized to provide clearance between the stylet lumen 100 and the coaxially inserted stylet wire 404 in the range from about 0.00025 cm (0.0001 inch) to about 0.025 cm (0.01 inch), and in some embodiments that clearance is about 0.0038 cm (0.0015 inches).

The conductor lumen 102 is formed in the internal portion 104 and positioned near an outer surface of the internal portion 104 such that there is only a web 110 between the conductor lumen 102 and the outer surface of the internal portion 104. Some embodiments have a plurality of conductor lumens 102 such as in the range from about two to sixteen conductor lumens 102. The implantable lead embodiment shown has four conductor assembly lumens that are substantially equidistant from each other and to the centrally localized stylet lumen. The conductor lumens 102 and stylet lumen 100 geometry provides axial stability, and the centrally located stylet lumen 100 improves navigation. Each conductor lumen 102 can be configured to resemble a polygon that is not necessarily symmetrical, and each conductor lumen 102 has a diameter typically greater than about 0.0254 cm (0.01 inch). In some embodiments, the conductor lumens 102 electrically insulate each conductor 34 and physically separate each conductors 34 to facilitate identification of the conductor 34 that is appropriate for its single corresponding contact 36. The film 108 thickness between the conductor lumens 102 and the stylet lumen 100 is no less than about 0.00254 cm (0.001 inch). This film 108 is flexible enough to allow the entering stylet to slide through the lead body without penetrating through into a conductor lumen 102 or out of the lead body.

The web 110 allows an axial slit 42 to be created in the internal portion 104 distal end for a path to exist between the conductor lumen 102 and the internal portion 104 outer surface. The web 110 is no greater than 0.005 cm (0.002 inch) thick. The web 110 provides the means for a conductor lumen 102 formed inside the lead body to be positioned near the exterior surface 44 of the lead body. The axial slit 42 is formed in the internal portion 104 distal end between the conductor lumen 102 and the outer surface of the internal portion 104. The axial slit 42 provides a temporary opening for a coupling 112 (FIG. 18) to exit the conductor lumen 102 and attach to a contact 36. The axial slit 42, when stretched ajar, opens to a width of at least about 0.01 cm (0.0039 inch) to allow the coupling 112 to exit the conductor lumen 102. Once the coupling 112 is connected to the contact 36, the axial slit 42 preferably seals back.

FIG. 6 shows an implantable lead with proximal end 38 enlargement indication embodiment, and FIG. 7 shows an enlarged cross section of the proximal end 38 shown in FIG. 6. An implantable lead with improved stylet lumen comprises a lead body, at least two conductors 34, contacts 36, and a proximal flare 200. The lead body has a proximal end 38, a distal end 40, a stylet lumen 100, and at least two conductor lumens 102. The conductors 34 are contained in the conductor lumens 102 extending from the lead proximal end 38 to the distal end 40. The contacts 36 are carried on the distal end 40 and electrically connected to the conductors 34. Typically, conductors 34 are also carried on the proximal end 38 and electrically connected to the conductors 34.

The proximal flare 200 is formed on the lead body proximal end 38 and it has tapering walls that narrow toward a stylet opening to guide insertion of a stylet (FIG. 10) into the stylet lumen 100, and the proximal flare 200 seals the conductor lumens 102 proximal end to isolate the conductor lumens 102. The proximal flare 200 is manufactured for a non-rigid material typically similar to the lead body material. The tapering walls have a slope typically in the range from about 0.25 cm/cm to about 0.50 cm/cm. The axial length of the flare 200 is no greater than about 0.064 cm (0.025 inches). The wall thickness of the flare 200 ranges from 0.01 cm (0.004 inch), at the most proximal end, to 0.05 cm (0.019 inch), at the distal end of the flare 200. The proximal flare 200 is flexible to reduce stylet deformation during insertion or withdrawal of the stylet. During stylet insertion into the stylet lumen 100, navigation, and withdraw, the tapered walls absorb energy and stretch to accommodate movement of the stylet to reduce stylet deformation. Also during stylet insertion into the stylet lumen 100, the proximal flare 200 substantially prevents the stylet from entering the conductor lumens 102. The flare 200 provides a progressive tactile feedback to indicate to the clinician the amount of stylet pressure being applying to the lead proximal end 38 which reduces lead/stylet damage or deformation during implant.

The proximal flare 200 seals the conductor lumens 102 proximal end to isolate the conductor lumens 102. The forming of the flare 200 places material in the conductor lumens 102 that typically extends no farther than the beginning of the conductors 34 located within the conductor lumens 102. Sealing the conductor lumens 102 minimize electrical conductance between the conductors 34, fluid migration into the lumens or other attached neurological devices, and unwanted stylet introduction into the conductor lumens 102. The proximal flare 200 is manufactured from a non-rigid material that can be the same material as the lead body. The flare 200 can be formed by inserting the proximal end 38 of the lead body into a mold that has a conical shape. This conical shape is inserted axially into the center stylet lumen 100. Heat is transferred from the conical mold to the polyurethane internal portion 104 that seals the outer lumens and creates the flare 200.

FIG. 8 shows an implantable lead with distal end 40 enlargement indication embodiment, and FIG. 9 shows an enlarged cross section of the distal end 40 shown in FIG. 8. An implantable lead with an improved distal tip 300 comprises a lead body, at least two conductors 34, contacts 36, a stylet lumen 100, conductor lumens 102, and a distal tip 300. The lead body has a proximal end 38, a distal end 40, a stylet lumen 100, and at least two conductor lumens 102. The at least two conductors 34 contained in the conductor lumens 102 extending from the lead proximal end 38 to the distal end 40. The at least two contacts 36 carried on the proximal end 38 are electrically connected to the conductors 34. The at least two contacts 36 carried on the lead distal end 40 are also electrically connected to the conductors 34.

The formed distal tip 300 seals the conductor lumens 102 free from adhesive or solvents. The conductor lumens 102 closed off by the formed distal tip 300 improve electrical isolation between the conductors 34. The formed distal tip 300 penetrates the lumens 100, 102 of the lead body. The material filling reaches no further into the lumens than making contact to the enclosed conductors 34.

The distal tip 300 can be formed from the lead body by inserting into a mold; this mold has the shape of the desired distal tip 300. The distal tip 300 has a diameter approximately equal to the lead final diameter of approximately 0.127 cm (0.05 inch). The heat conducted from the mold to the lead distal tip 300, melts the surrounding material into the conductor lumen 102 and into the stylet lumen 100, completely sealing them from the outside. Sufficient material is left between the lumens 100, 102 to the outside of the lead such that substantial force would be needed to perforate, if at all, through the finally formed distal tip 300. The formed distal tip 300 is of the same material of the lead body and significantly minimizes the possibility of separation from the lead body.

The distal tip 300 is substantially symmetrical since there is no need to align a separate distal tip 300. The distal tip 300 is symmetrically formed such that it is coaxial with the lead body. Symmetry is desirable for minimized protuberances from the exterior lead surface 44, thus reducing the potential of lead body ruptures. The symmetrical formation of the distal tip 300 also reduces physical and material discontinuities in the distal tip 300 to improve the navigational sensitivity of the lead 30 during implant potentially reducing operating room time.

The distal tip 300 is a more robust stylet stop, which reduces the opportunity for stylet penetration of the lead body distal end 40. The material penetrates the most distal end of the stylet lumen 100 by about 0.15 cm (0.059 inch) into the stylet lumen 100 of the lead beginning from the most distal end of the hemi-spherical distal tip 300. The force transfer required for perforation of the lead distal end 40 is significantly increased, therefore, reducing any potential of tissue damage due to an exiting stylet and reducing the potential of creating an opening in the lead which may disable electrical properties of the device.

FIG. 10 shows a stylet with stylet distal end 400 enlargement indication embodiment, and FIG. 11 shows the enlarged distal end shown in FIG. 10. An implantable lead with an improved stylet comprises a lead body, a stylet lumen 100, at least one conductor 34, contacts 36, and a stylet. The lead body has a proximal end 38, a distal end 40, an exterior surface 44, and a stylet lumen 100 contained inside the lead body. The conductor 34 is contained in the lead body and generally extends from the lead proximal end 38 to the distal end 40. The conductor 34 is electrically insulated by the lead body. There is at least one contact 36 carried on the lead proximal end 38 that is electrically connected to the conductor 34, and there is at least one contact 36 carried on the lead distal end 46 that is electrically connected to the conductor 34.

The stylet is composed of a stylet handle 402 that attaches to the proximal end 38 of the lead and a stylet wire 404. The stylet wire 404 is configured for insertion into the stylet lumen 100 with a straight portion 406, a curved portion 408, and a ball tip 410 on the stylet distal end 400. The straight portion of the lead has a diameter of about 0.0254 cm (0.01 inch) and has a parylene insulation of about 1.0 micron. The electrical insulation also serves as a coating that has a lower coefficient of friction than the stainless steel of the stylet wire 404.

The curved portion of the stylet wire 404 has an angle, between the tangent of the curved portion and the straight portion that increases as the curve approaches the stylet distal end 400. The curved portion begins at about less than 3.75 cm (1.48 inches) from the stylet distal end 400 of the stylet wire 404. The most distal angle of the curved portion has an angle greater than about 15 degrees from the straight portion.

The tangent of the curve with respect to the straight portion of stylet increases linearly as the curve approaches the stylet distal end 400. Once fully inserted into the lead, the stylet/lead results in a distal end angle that allows the physician to manipulate the device into the desired location over the epidural space. The continuous and incremental curve of the lead distal tip 300 aids the physician to guide the lead past anatomical obstructions, that would otherwise, hinder the ease of introduction of the lead to its designated location for stimulation.

The ball tip 410 is spherical and has a diameter that is greater than the stylet diameter and is no greater than the stylet lumen 100 inner diameter. The ball tip 410 is configured to ease insertion of the stylet wire 404 through the stylet lumen 100 to the stylet distal end 400. The ball tip 410 functions by stretching the lumen where the stylet wire 404 is inserted to ease insertion of the remaining portion of the stylet wire 404. In addition, the ball tip 410 reduces abrasion to the stylet lumen 100 to reduce the risk of the stylet wire 404 protruding into the adjacent conductor lumens 102 or out of the exterior surface 44 of the lead body.

FIG. 12 shows an implantable lead with contact 36 enlargement indication, and FIG. 13 shows a cross section of an enlarged contact 36 embodiment. The coupling 112 has a conductor coupling 500 and a contact coupling 502. The conductor coupling 500 and the contact coupling 502 are manufactured from a material with good mechanical and electrical properties such as MP35N and the like. The conductor coupling 500 is placed over the conductor 34 and attached to the conductor 34 mechanically. The contact coupling 502 exits the lead body and has a weld 504 to connect the contact coupling 502 to the contact 36. The weld 504, such as a laser weld, can be performed substantially on the contact 36 exterior surface 44 for ease of manufacturing. The weld 504 is performed such that the weld 504 pool is typically contained within the contact 36 perimeter. In addition, the weld 504 height is controlled to be less than about 0.0127 cm (0.005 inch), so interaction with other devices is facilitated. Each contact 36 has a contact slot 508 opening that in some embodiment is in the range from about 0.0127 cm (0.005 inch) to about 0.0381 cm (0.015 inch) in width and at least about 0.0508 cm (0.020 inch) in length. In other embodiments, the contact slot 508 can extend the entire length of the contact 36.

An isolation space 506 is created between the conductor 34 and the contact 36 to prevent directly welding the conductor 34 to the contact 36. The isolation space 506 separates the conductor 34 from the weld 504 to substantially prevent the conductor 34 from contacting the weld 504. The isolation space 506 is necessary since silver is not wanted in the weld 504 pool because silver potentially weakens the strength and integrity of a weld 504. In addition, it is desirable to avoid having silver contact the outside surface of the lead to avoid any direct contact with tissue. Although silver contact with tissue is not considered harmful, the separation serves as an additional precaution. The isolation space 506 is greater than about 0.05 cm (0.02 inch). The isolation space 506 serves as a means for isolation created between the conductor 34 and the contact 36 to prevent directly welding the conductor 34 to the contact 36. In some embodiments, the isolation space can include a fill material such as epoxy.

Figure 15:
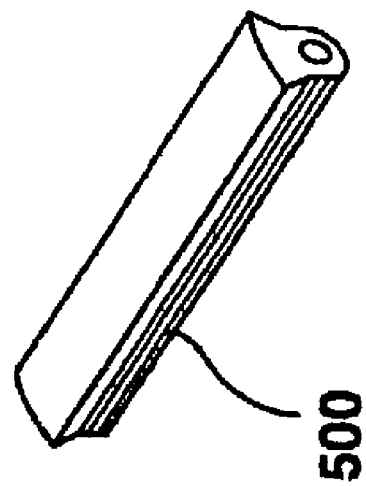
FIG. 15 shows an isometric view of the coupling embodiment shown in FIG. 14.
Figure 14:
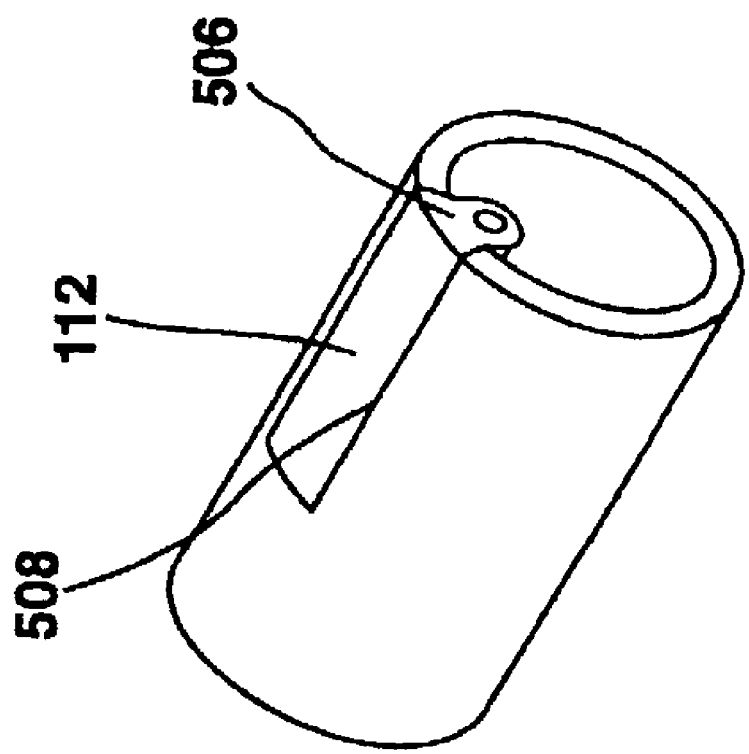
FIG. 14 shows an isometric view of a contact and coupling embodiment.

FIG. 14 shows an isometric view of a contact 36 and coupling 112 embodiment, and FIG. 15 shows an isometric view of the coupling 112 embodiment shown in FIG. 14. In this embodiment, the isolation space 506 is provided by the specific geometry of the contact coupling 502 and more specifically the non-welded material between the conductor 34 and the weld 504 to the contact 36. The non-welded material is sized appropriately for the dimensions of the lead such as greater than about 0.005 cm (0.002 inches). In this embodiment, the interface between the outer surface of the contact 36 and the other surface of the coupling 500 can be continuously welded along selected sides of the interface or intermittently welded along the interface.

Figure 16:
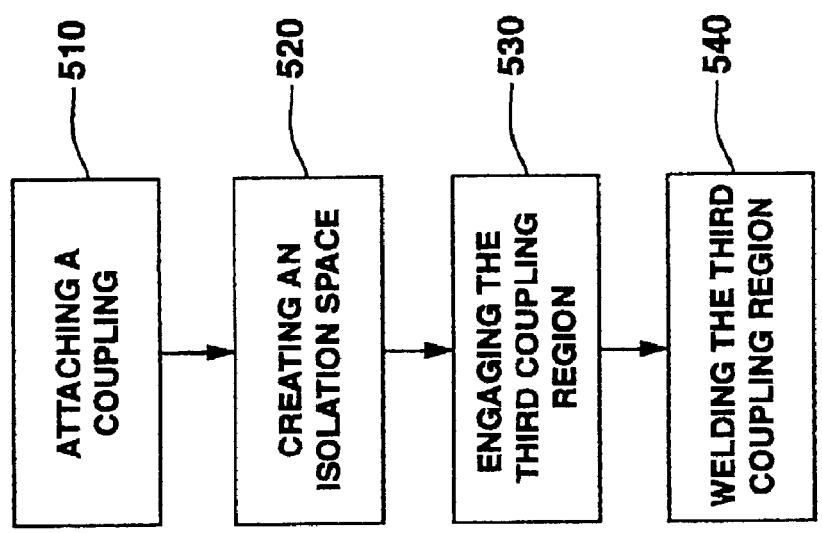
FIG. 16 shows a flow chart of a method for creating an isolation space in an implantable lead contact connection embodiment; and, FIG. 17 shows a flow chart of a method for creating a coplanar connection in an implantable lead between a conductor and a contact embodiment.

FIG. 16 shows a flow chart of a method for creating an isolation space 506 in an implantable lead contact connection embodiment. The method for creating an isolation space 506 comprises the following elements. A coupling 112 is attached 510 to a conductor 34 so that the conductor 34 extends into a first coupling region 500 of the coupling 112. The coupling 112 has a second coupling region 506 that is adjacent to the first coupling region 500 and a third coupling region 502 adjacent to the second coupling region 506. An isolation space 506 is created 520 and formed by the second coupling region 506. The isolation space 506 is void of the conductor 34. The third coupling region 502 is engaged 530 into a contact slot 508 formed in a contact 36. The third coupling region 502 is welded 540 to the contact 36 creating a contact weld 504.

In the coupling 112 embodiment shown in FIG. 13, the method for creating an isolation space 506 in an implantable lead contact connection is performed as follows. A coupling 112 is attached to a conductor 34 distal end so that a first coupling region 500, a second coupling region 506, and a third coupling region 502 are formed. The first coupling region 500 is mechanically attached to the conductor 34 in a crimping process that substantially reduces the diameter of the first coupling region 500 such that it engages the conductor 34 firmly. During mechanical attachment, the crimping force is adjusted to obtain an adequate pull strength while avoiding undesired damage/deformation to the wire 404. The conductor 34 distal end extends into the first coupling region 500 of the coupling 112. The second coupling region 506 is distal to the first coupling region 500, and the third coupling region 502 is distal to the second coupling region 506. The first region can be about 0.10 cm (0.04 inch) long, the second region can be about 0.05 cm (0.02 inch) and the third region can be about 0.076 cm (0.03 inch) long. An isolation space 506 is created and formed by the second coupling region 506, with the isolation space 506 void of the conductor 34. The isolation space 506 is void of the conductor 34 so that the weld 504 encompasses the third region and the contact 36.

The assembly consisting of the conductor 34 and the attached couplings 112 on either end can be fed through a lead body. The placement of the assembly is such that the proximal coupling is on the proximal end 38 of the lead body and the distal coupling is on the distal end of the lead body. The contact 36 with a contact slot 508 is placed on the lead body distal end. The contact slot 508 width is slightly less than the diameter of the third coupling region 502. The length of the contact slot 508 is greater than the diameter of the coupling 112 to allow for placement anywhere along its length. The contact slot 508 assists in holding the coupling 112 in place prior to welding the third region to the contact 36.

An axial slit 42 is created in the lead body distal end. The axial slit 42 is long enough such that it allows for an opening of at least the diameter of the third coupling region 502. The coupling 112 attached to the conductor 34 is exited through the axial slit 42 in the lead body distal end. The axial slit 42 permits the coupling 112 to pass through to mate to the contact 36 with the minimum amount of movement of the conductor 34 assembly within the lead body. Also, the axial slit 42 allows for a minimum sized path to exist between the conductor lumen 102 and the contact 36. In the creation of the axial slit 42, material is not removed, only a cut is made such that it allows the passage of the coupling 112 from the conductor lumen 102 to the contact slot 508 area. The cut is created with a sharp razor and extends for about 0.076 cm (0.030 inch). It is made approximately under the location where the contact 36 will be placed over and mate with the coupling 112.

The third coupling region 502 is bent in the range from about 85 degrees to about 120 degrees in relation to the longitudinal axis of the conductor 34. The bend can be made with a tool the size of a wrench that creates a bend beginning at the same location of the coupling 112, roughly 0.076 cm (0.03 inch) distally. The third coupling region 502 distal end is formed into a contact coupling 502 that is complimentary to a contact slot 508. The diameter of the third coupling region 502 is deformed such that it closes the conductor 34 void opening of the third coupling region 502. Also, the formed final geometry of the third region of the coupling 502 has an interference fit with the contact slot 508.

The contact coupling 502 is engaged into the contact slot 508. The entire perimeter and cross section of the third region 502 is placed within the open area of the contact slot 508. At this point the third coupling region 502 is held by the contact slot 508 and is ready for a more secure attachment. The contact coupling 502 is welded to the contact slot 508. The weld 504 can be created with a laser welder that heats up the slot 508 region of the contact 36 and the third region of the coupling to the point where they become an alloy. The weld 504 bump created is no greater than about 0.013 cm (0.005 inch) over the surface of the contact 36. Also, the weld 504 bridges over each end of the slot 508 to provide mechanical integrity. The inner void of the third coupling region 502 distal end is sealed by the weld 504. The weld 504 surface area extends over the third region 502 of the coupling and the proximate perimeter of the contact slot 508. The weld 504 material creates a closed section in the third region 502 opening creating a closed section of the coupling distal end (third coupling region 502).

FIG. 12 shows an implantable lead with contact enlargement indication, and FIG. 13 shows a cross section of an enlarged contact embodiment. An implantable lead with coplanar contact connection comprises a lead body having a proximal end 38 and a distal end 40, at least one conductor 34, at least one contact 36 carried on the proximal end 38, at least one contact 36 carried on the distal end 40, and at least one coupling 112. The lead body 32 has an exterior surface 44. The conductor 34 is contained in the lead body 32 and extends generally from the lead proximal end 38 to the distal end 40. The conductor 34 is electrically insulated. There is at least one contact 36 carried on the proximal end 38 that is electrically connected to the conductor 34, and at least one contact 36 carried on the distal end 40 that is electrically connected to the conductor 34. The coupling 112 has a conductor coupling 500 and a contact coupling 502. The conductor coupling 500 is placed over the conductor 34 and attached to the conductor 34. The contact coupling 502 exits the lead body and is welded to connect the contact coupling 502 to the contact 36 carried on the distal end 40. The contact coupling 502 is further configured to exit the conductor lumen 102 and mate with the contact 36 while retaining the conductor 34 coplanar to the contact 36. The coplanar relationship between the conductor 34 and the contact 36 is such that the longitudinal axis of the conductor 34 is maintained substantially parallel to the longitudinal axis of the contact 36.

In some embodiments such as shown in FIG. 13, the contact coupling 502 can be bent to exit the conductor lumen 102 and mate with the contact 36 while maintaining the conductor 34 coplanar to the contact 36. The contact coupling 502 bend serves as a means for orienting the contact coupling 502 to exit the conductor lumen 102 and mate with the contact 36. The contact coupling 502 can be bent in the range from about 85 degrees to about 120 degrees in relation to the conductor 34. In other embodiments such as shown in FIGS. 14 and 15, the geometry of the contact coupling 502 is such that the contact coupling 502 does not require mechanical deformation of the second region 506 or third region; 502.

The conductors 34 are contained within the lumens throughout the lead body, such that it does not exit the lead at any point. The conductor 34 is parallel to the lead body in its entire length. This allows the conductor 34 to not directly contact the outside surface of the lead or the surrounding tissue. Conductor 34 stresses are significantly reduced by not allowing the conductor 34 to have a bending moment. Lead reliability is improved as a result from this coplanar conductor 34 to contact 36 attachment.

Figure 17:
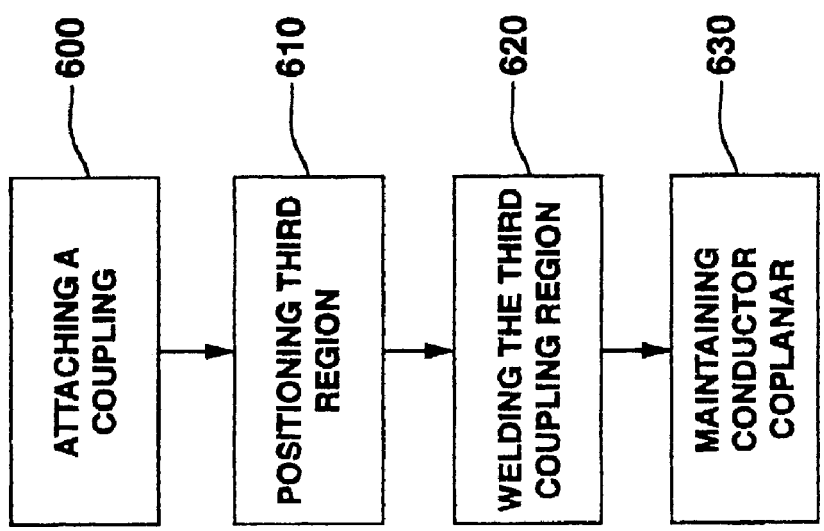

FIG. 17 shows a flow chart of a method for creating a coplanar connection in an implantable lead between a conductor 34 and a contact 36 embodiment. The method for creating a coplanar connection in an implantable lead between a conductor 34 and a contact 36 comprises the following elements. A coupling 112 is attached 600 to a conductor 34 distal end, so the conductor 34 distal end extends into a first coupling region 500 of the coupling. The coupling 112 has a second coupling region 506 adjacent to the first coupling region 500. The coupling second region 506 is positioned 610 in a conductor lumen 102 adjacent 620 to a contact 36. The second region 506 is welded 62 to the contact 36 creating a contact weld 504. The conductor 34 distal end is maintained in a coplanar relation 630 to the contact 36.

Figure 18:
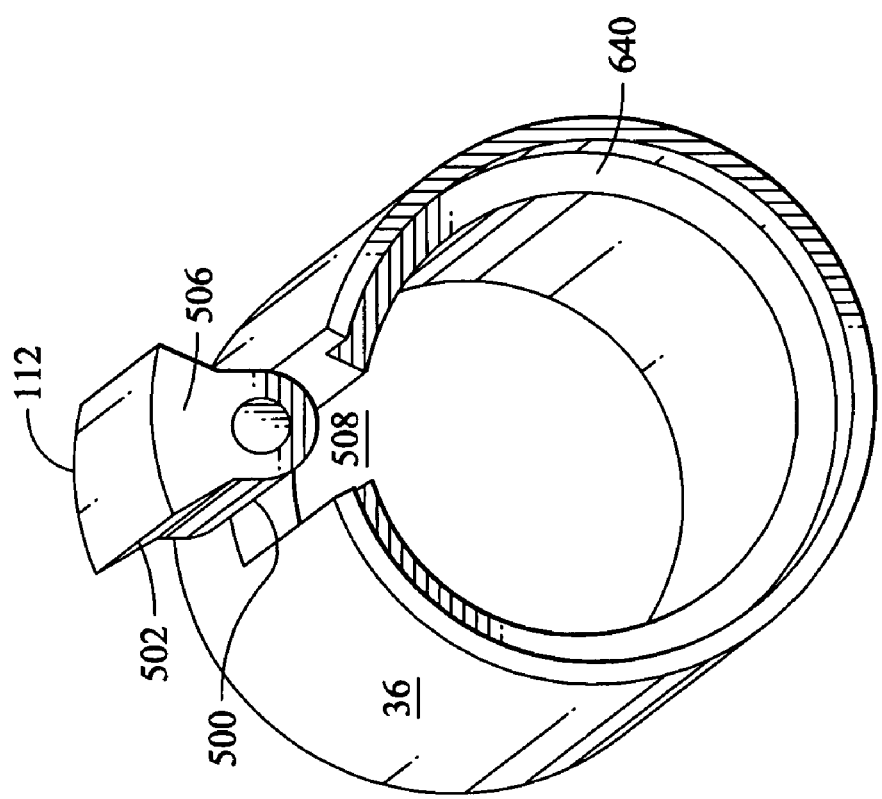
FIG. 18 shows an isometric view of a contact and coupling embodiment.

FIG. 18 shows an isometric view of another contact 36 and coupling (or crimp sleeve) 112 Embodiment providing a coplanar contact connection. This embodiment is comprised of contact 36, coupling 112, conductor coupling 500, contact coupling 502, contact slot 508, and counter-boar 640. Contact 36 and coupling 112 are manufactured from a material with good mechanical and electrical properties. In a preferred embodiment all contacts 36 and couplings 112 carried on distal end 40 are comprised of a platinum-iridium alloy. More specifically it is preferred that all contacts 36 and couplings 112 carried on the distal end are comprised of a platinum-iridium alloy that is 90% platinum and 10% iridium. The platinum-iridium alloy provides a highly conductive and corrosion resistant electrical contact. Further, in a preferred embodiment all contacts 36 and couplings 112 carried on the proximal end are comprised of MP35N to provide reliable contact when proximal end 38 is inserted into a neurostimulation system extension or neurostimulator. MP35N is used for the proximal end contacts 36 and couplings 112 because it is stronger than most metals which makes contacts 36 and couplings 112 more resistive to damage when the implantable lead is utilized with neurostimulation systems which utilize set screws to hold the implantable lead within the stimulation lead extension or neurostimulator. However, it is fully contemplated that contacts 36 and couplings 112 carried on proximal end 38 and 40 can be of any type of electrically conductive material which can provide a low impedance electrical connection. Further, contact 36 can be of any dimension, however, contact 36 preferably has an outer radius of 0.127 cm (0.050 inches), an inner radius of 0.102 cm (0.040 inches), and an inner radius of the counter-boar 640 of 0.122 cm (0.048 inches). The preferred dimensions of coupling 112 are discussed further below.

Figure 19:
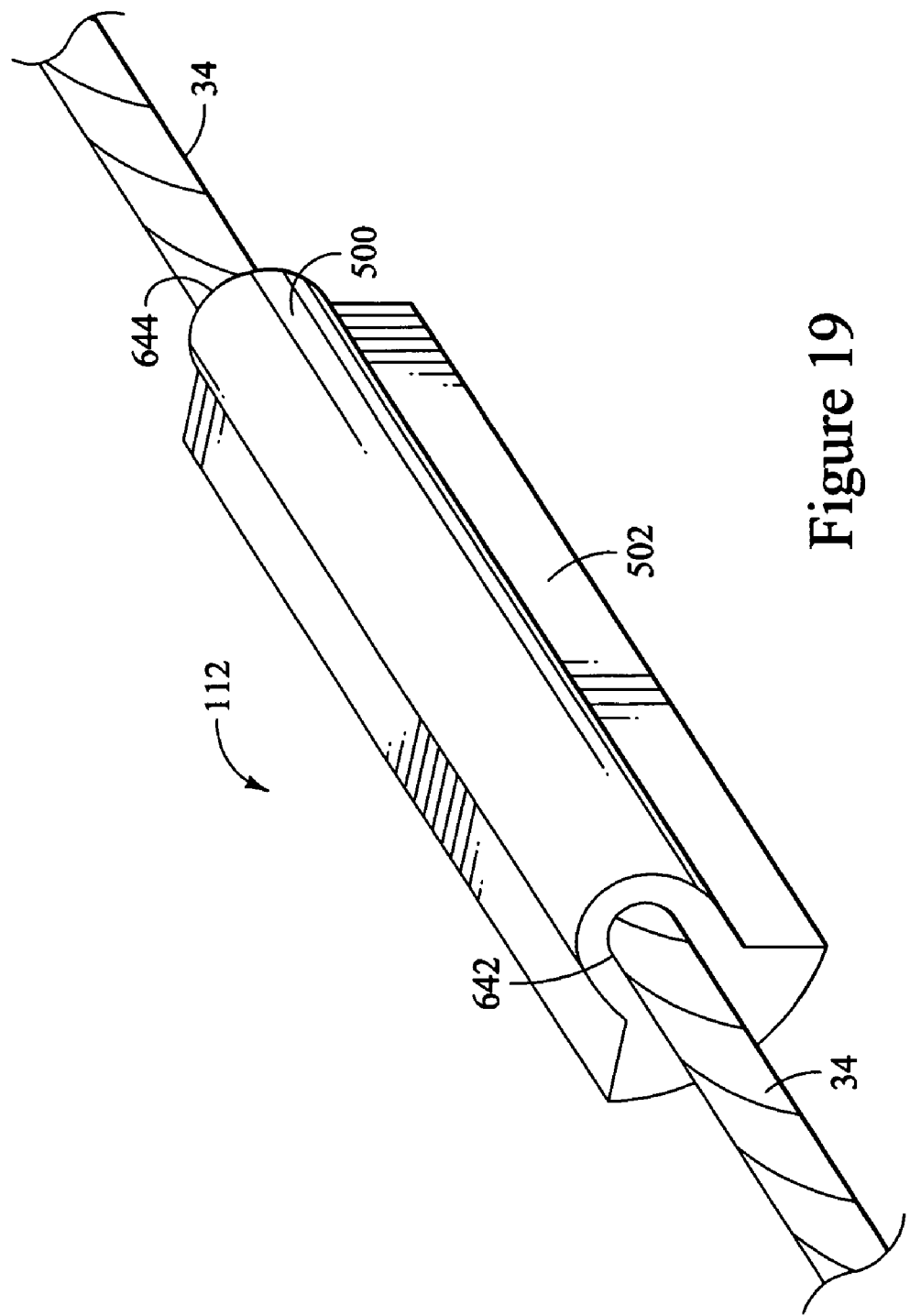
FIG. 19 shows a connection embodiment between a conductor and a coupling.

With reference to FIGS. 12 & 19 conductor coupling 500 of coupling 112 is placed over conductor 34. Conductor 34 preferably enters a first end 642 and exits a second end 644 and then is attached to conductor 34. There are many ways to attach conductor coupling 500 to conductor 34, however, it is preferred if the attachment is not by welding to prevent any heat damage to conductor 34. It is further preferred if the attachment is performed by crimping to create a reliable attachment. After attachment any portion of conductor 34 extending past second end 644 is preferably removed or cut away so that conductor 34 is flush with the end of second end 644. It is also contemplated that conductor 34 need not exit second end 644. Conductor 34 could extend into conductor coupling 500 either partially or fully and still be within the scope of the present invention.

Figure 20:
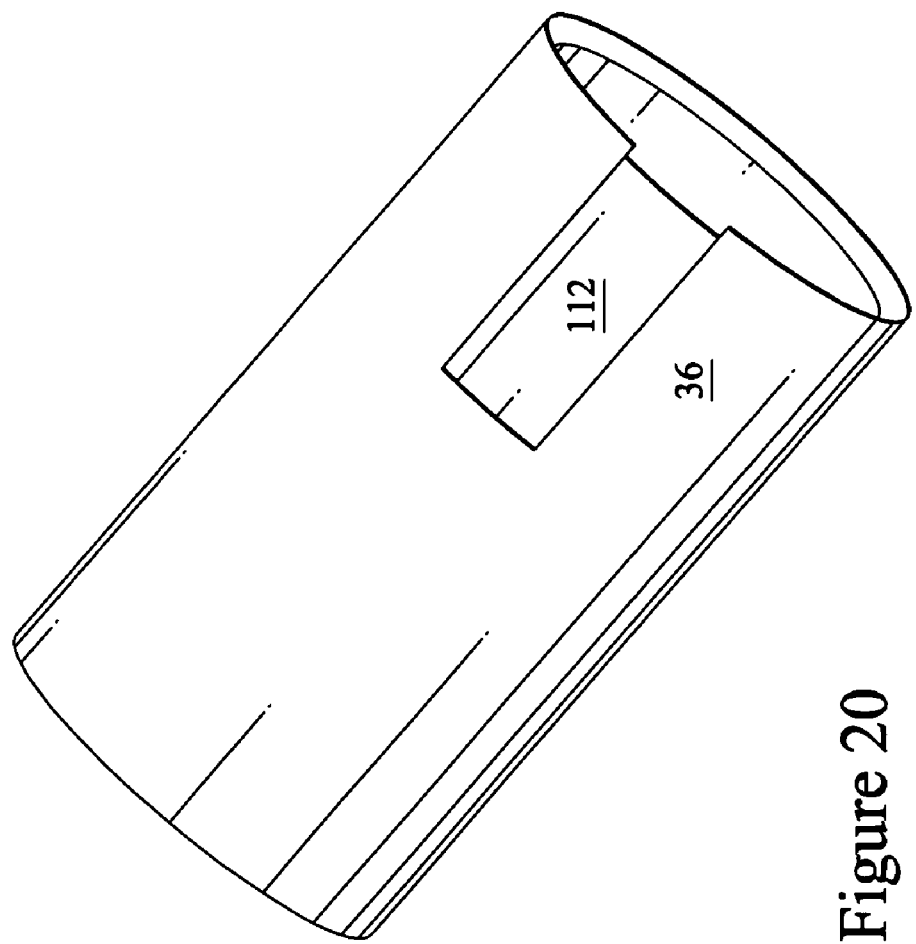
FIG. 20 shows an elevated top view of the contact and coupling embodiment of FIG. 18.

With reference to FIG. 20, coupling 112 is then placed into contact slot 508 in direct contact with contact 36. For the following discussion, length is defined as a dimension substantially parallel to the longitudinal axis of contact 36. In a preferred embodiment, coupling 112 has a smaller length than the length of contact slot 508. This allows for coupling 112 to be placed anywhere along the length of contact slot 508, which makes the connection of contact coupling 502 and contact 36 more accommodating for manufacturing imperfections in the conductor length. Typically conductors are designed at very specific length tolerances to eliminate bending moments and tensile and stresses created by bending or stretching the conductor caused by an overly long or an overly short conductor respectively. However, due to manufacturing imperfections, conductors can be cut longer or shorter based on the conductor length tolerances. By sliding coupling 112 along the length of contact slot 508 conductor length imperfections can be overcome to further reduce any conductor bending moments or tensile stresses. In a preferred embodiment coupling 112 is 0.025 cm (0.010 inches) shorter than the length of contact slot 508. However, it is contemplated that coupling 112 can be any length up to and including longer than contact slot 508.

Figure 21:
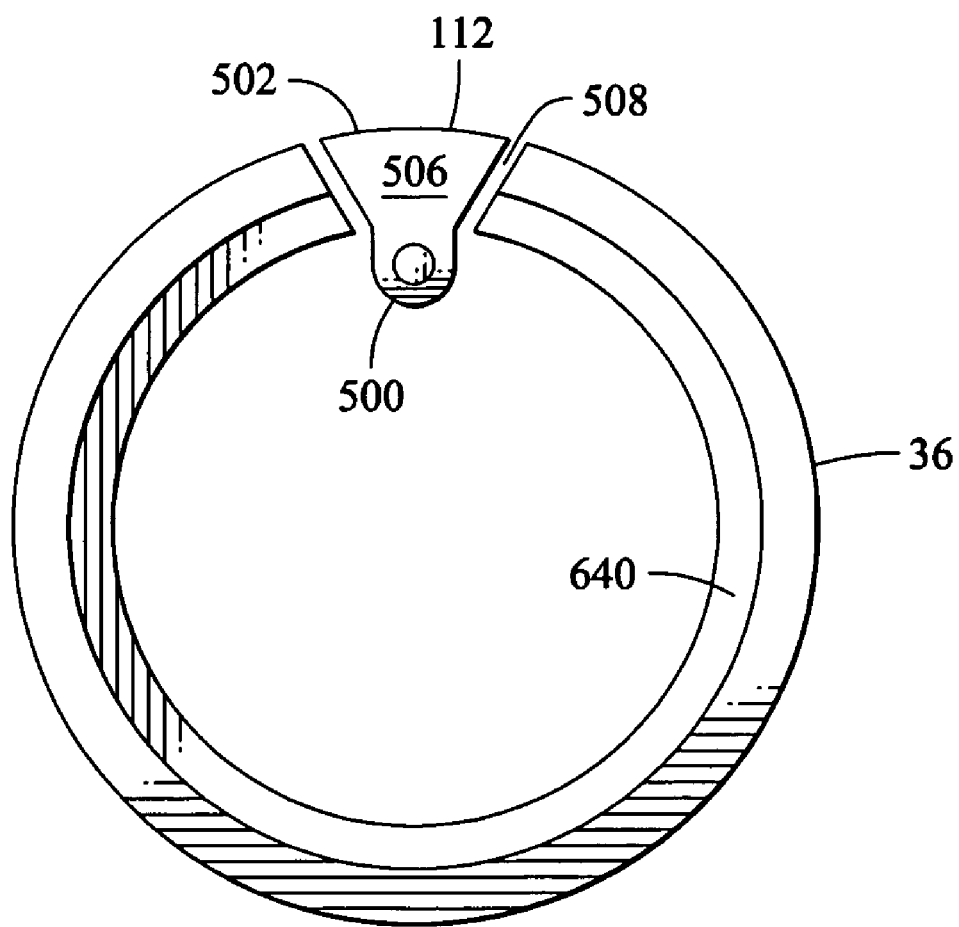
FIG. 21 shows a front profile view of the contact and coupling embodiment of FIG. 18.

With reference to FIG. 21, a front profile view shows the interconnection between coupling 112 and contact 36. As is shown, contact slot 508 narrows from the outer diameter of contact 36 to the inside diameter of contact 36. In a preferred embodiment, contact slot 508 narrows from a dimension of approximately 0.036 cm (0.014 inches) on the outer diameter of contact 36 to approximately 0.023 cm (0.009 inches) on the inside diameter of contact 36. As is also shown, contact coupling 502 narrows from the outer edge of contact coupling 502 to conductor coupling 500. In a preferred embodiment, contact coupling 502 narrows from a dimension of approximately 0.038 cm (0.015 inches) on the outer diameter of contact coupling 502 to approximately 0.025 cm (0.010 inches) at conductor coupling 500. The angled design of both contact slot 508 and contact coupling 502 allows for coupling 112 to rest within contact slot 508 without falling through contact slot 508 or without having to be held in place during the attachment of coupling 112 to contact 36. It is this connection, which allows for conductor 34 to be substantially coplanar with contact 36. This coplanar connection eliminates any unnecessary bending moments, which can reduce; the reliability and useful life of conductor 34. Further, conductor 34 remains entirely within the implantable lead reducing any concerns with conductor-patient contact.

Figure 22:
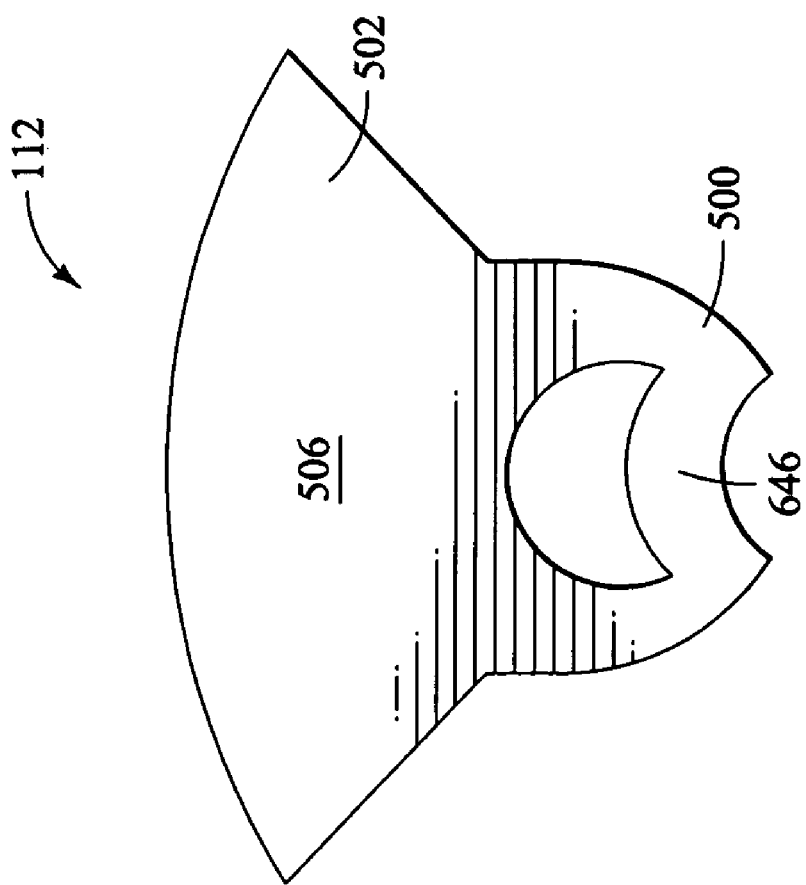
FIG. 22 shows a front profile view of a coupling embodiment.

With reference to FIGS. 21 & 22, coupling 112 is shown after conductor 34 has been attached. In this embodiment coupling 112 has been crimped to conductor 34. Crimp 646 is preferably made at the bottom of conductor coupling 500 to ensure no deformities in the sides of conductor coupling 500, which can result from crimping. Crimping conductor coupling 500 from the bottom prevents the sides from becoming distended and thus coupling 112 would be unable to rest substantially isodiametrically within contact slot 508 as shown in FIG. 21. However, it is contemplated that conductor coupling 500 could be crimped from the sides, but the preferred method is crimping from the bottom of conductor coupling 500. Other methods of attaching conductor coupling 500 to conductor 34 are contemplated such as adhering conductor coupling 500 to conductor 34 with a conductive glue or providing an inner catch within conductor coupling 500 that allows conductor 34 to enter conductor coupling 500 but prevents withdrawal of the conductor.

Figure 23:
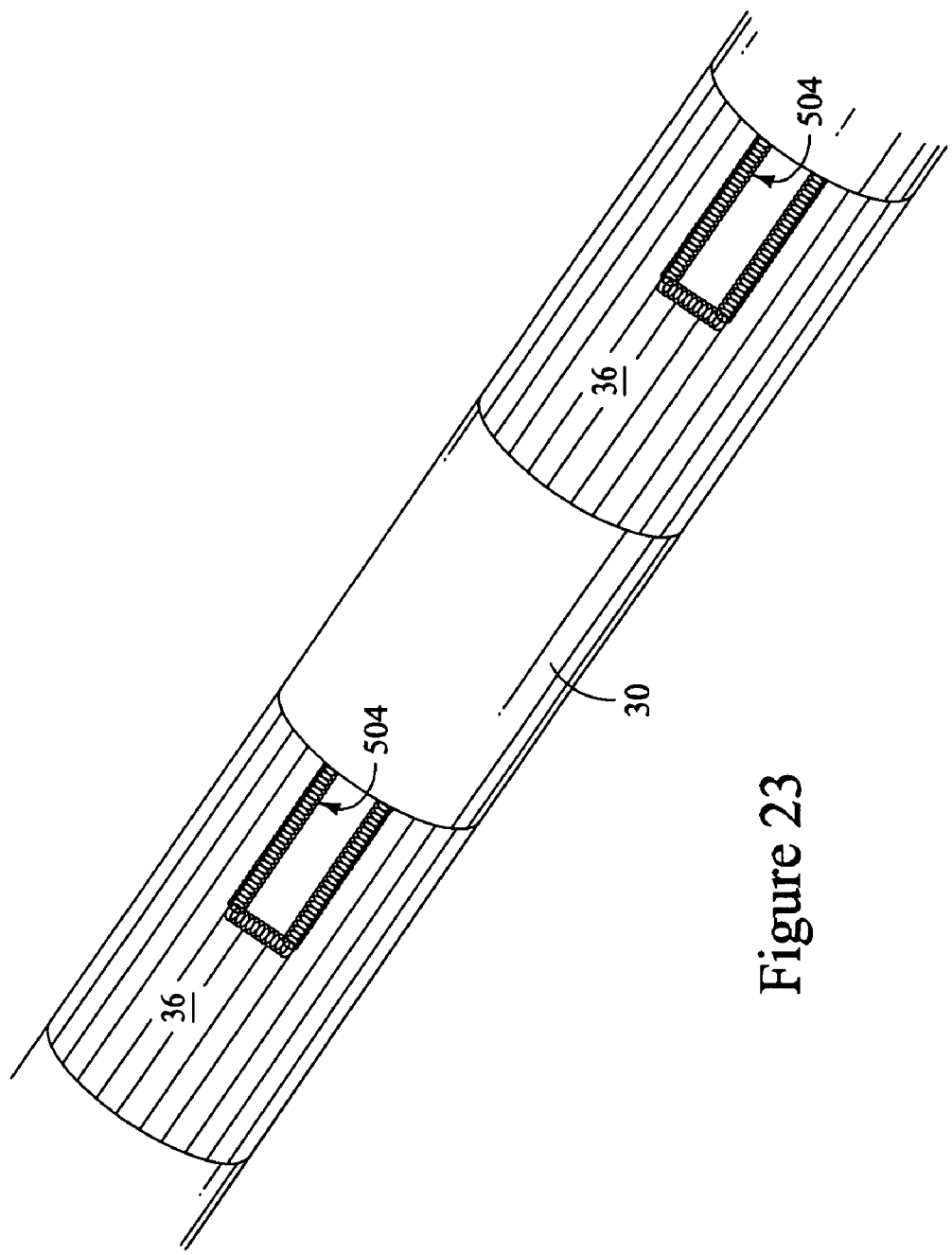
FIG. 23 shows a section of an implantable lead with contacts.

With respect to FIG. 23, an implantable lead is shown with contacts 36 attached thereto. As is shown, once coupling 112 is placed within contact slot 508 and is in a position to prevent conductor bending moments or stress from stretching, then outside surface of contact coupling 502 is welded to the outside surface of contact 36 as represented by contact weld 504. The weld 504 is performed such that the weld 504 pool is typically contained within the contact 36 perimeter. In addition, the weld 504 height is controlled to be less than about 0.0127 cm (0.003 inch), so interaction with other devices is facilitated. Each contact 36 has a contact slot 508 opening that in some embodiment is in the range from about 0.0127 cm (0.005 inch) to about 0.0381 cm (0.015 inch) in width and at least about 0.0508 cm (0.020 inch) in length. In other embodiments, the contact slot 508 can extend the entire length of the contact 36 as is discussed in more detail below.

Figure 24:
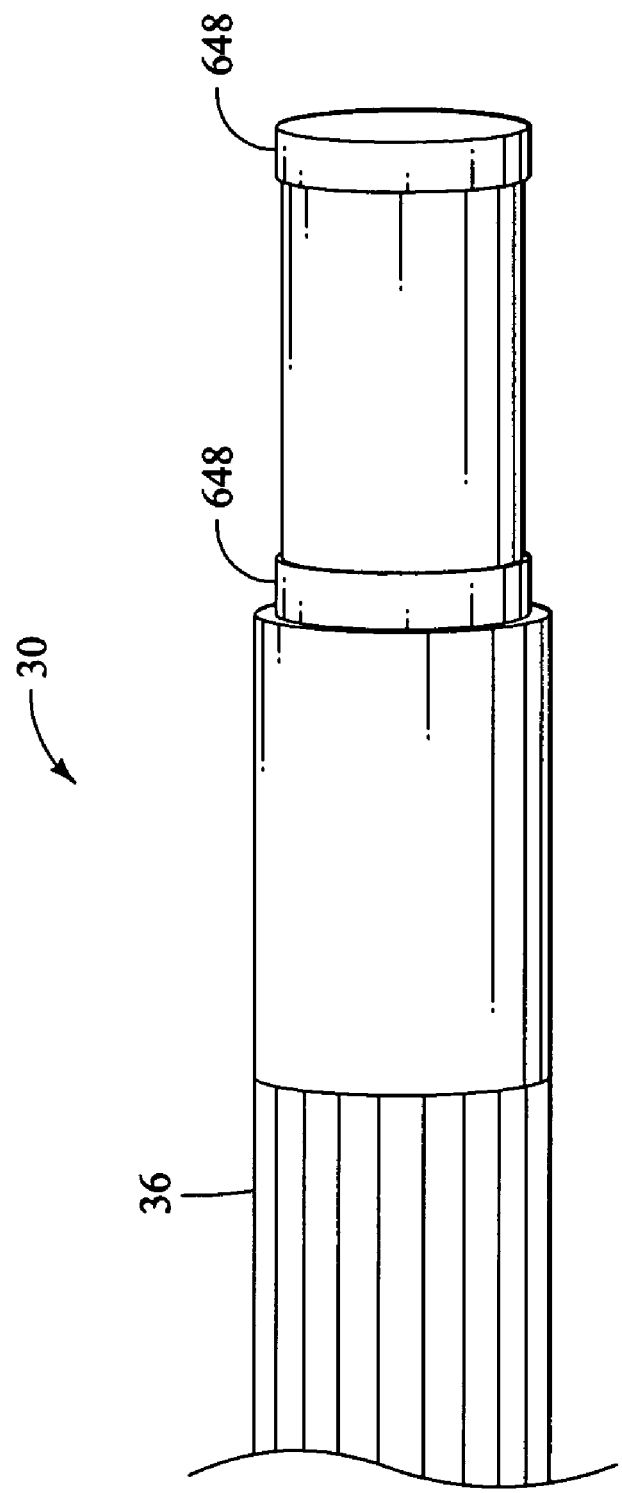
FIG. 24 shows an implantable lead with an end contact removed.
Figure 25:
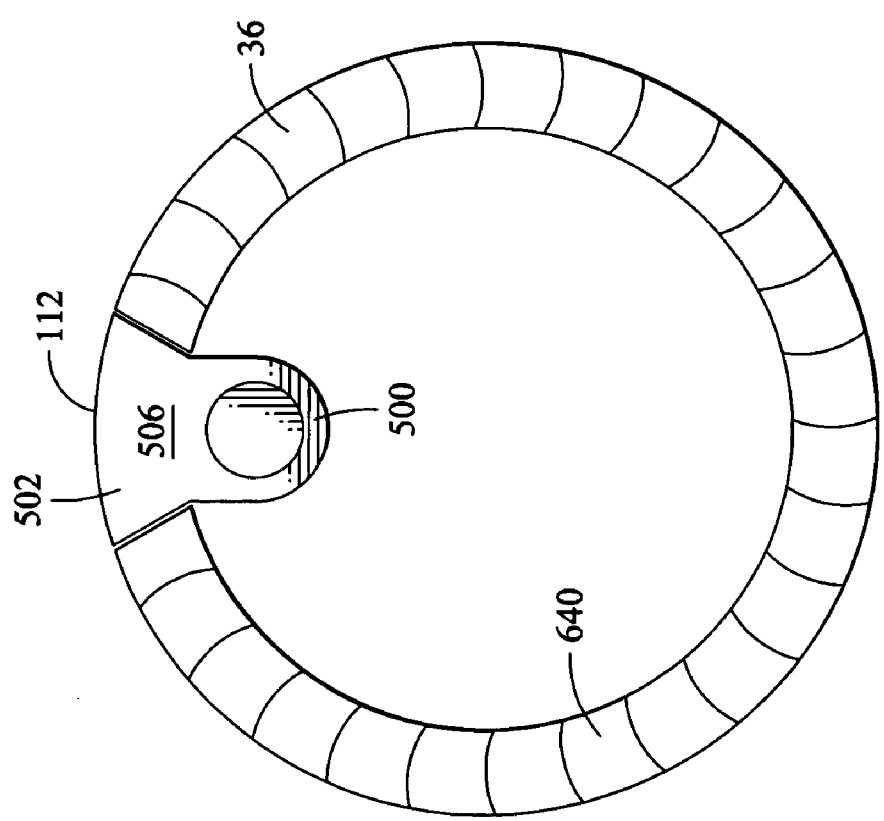
FIG. 25 shows another contact embodiment.

With respect to FIG. 24, an implantable lead is shown with the end contact removed. As shown, ridges 648 in the implantable lead mold will rest inside of counter-bore 640 on contact 36. Ridges 648 and counter-bore 640 together prevent contact 36 from moving axially and radially along the implantable lead. Any pressure on contact 36 to move in an axial direction is prevented by ridge 648 making contact with counter-bore 640. Further, with respect to FIG. 25 an alternative embodiment for contact 36 is shown where counter-bore 640 is rounded from the outer diameter of contact 36 inward to the inner diameter of contact 36. In both embodiments, counter-boar 640 preferable extends lengthwise into contact 36 0.025 cm (0.010 inches). Counter bore 640 offers a manufacturing advantage in that if the interior of lead 30 is to be filled with an insulative material (e.g., epoxy), counter boar 640 keeps the insulative material from leaking out at the edges of contact 36 during the filling process.

With reference again to FIG. 18, contact coupling 502 is configured to mate with contact 36 while retaining the conductor 34 coplanar to the contact 36. The coplanar relationship between conductor 34 and the contact 36 is such that the longitudinal axis of the conductor 34 is maintained substantially parallel to the longitudinal axis of the contact 36. The geometry of contact coupling 502 is such that contact coupling 502 does not require mechanical deformation. Therefore, conductors 34 are contained within the lumens throughout the lead body, such that it does not exit the lead at any point. Conductor 34 is essentially parallel to the lead body in its entire length. This allows conductor 34 not to directly contact the outside surface of the lead or the surrounding tissue. Conductor 34 stresses are significantly reduced by not allowing conductor 34 to have a bending moment. Therefore, lead reliability is improved as a result from this coplanar conductor 34 to contact 36 attachment.

Figure 26:
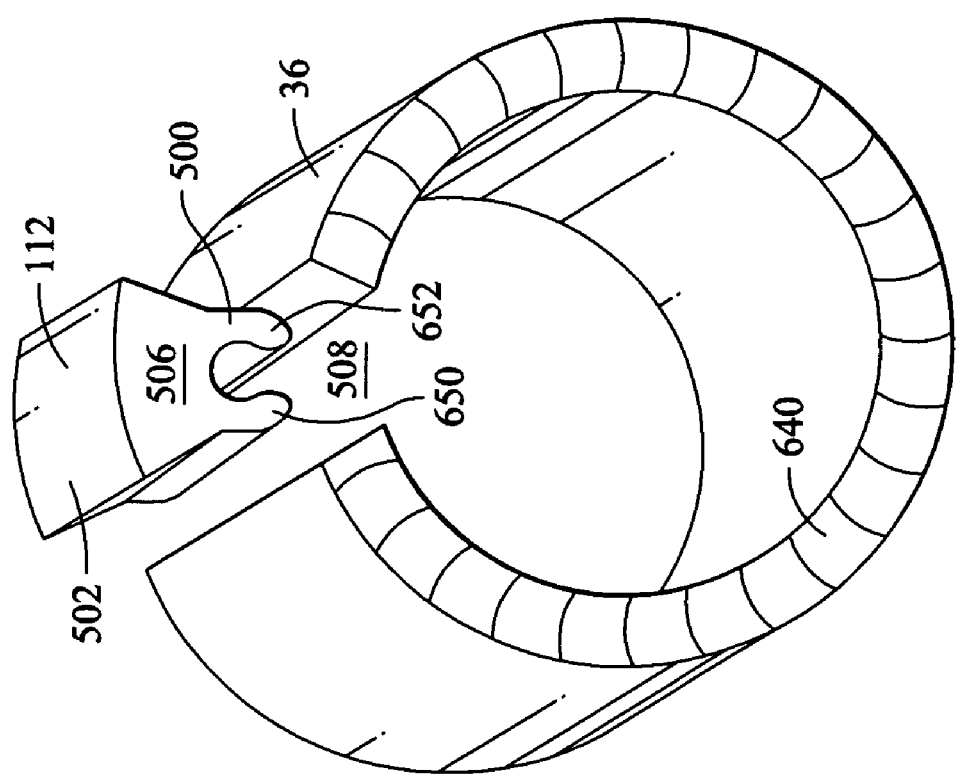
FIG. 26 shows another contact embodiment.

FIG. 26 shows another embodiment for contact 36 and coupling 112. In this embodiment a "wisdom tooth" design is shown. Conductor coupling 500 is made up of two side arms 650 and 652. When conductor coupling 500 is placed over conductor 34, side arms 650 and 652 are crimped inward to securely hold conductor 34 substantially coplanar with contact 36. Further, as mentioned above conductor 34 could be retained within conductor coupling 500 with conductive glue or any other means of secure attachment. Coupling 112 is then placed in contact slot 508 and then attached to contact 36. Further, as is shown, contact slot 508 extends the entire length of contact 36. This allows more room in which to place coupling 112 and reduces manufacturing costs.

Figure 27:
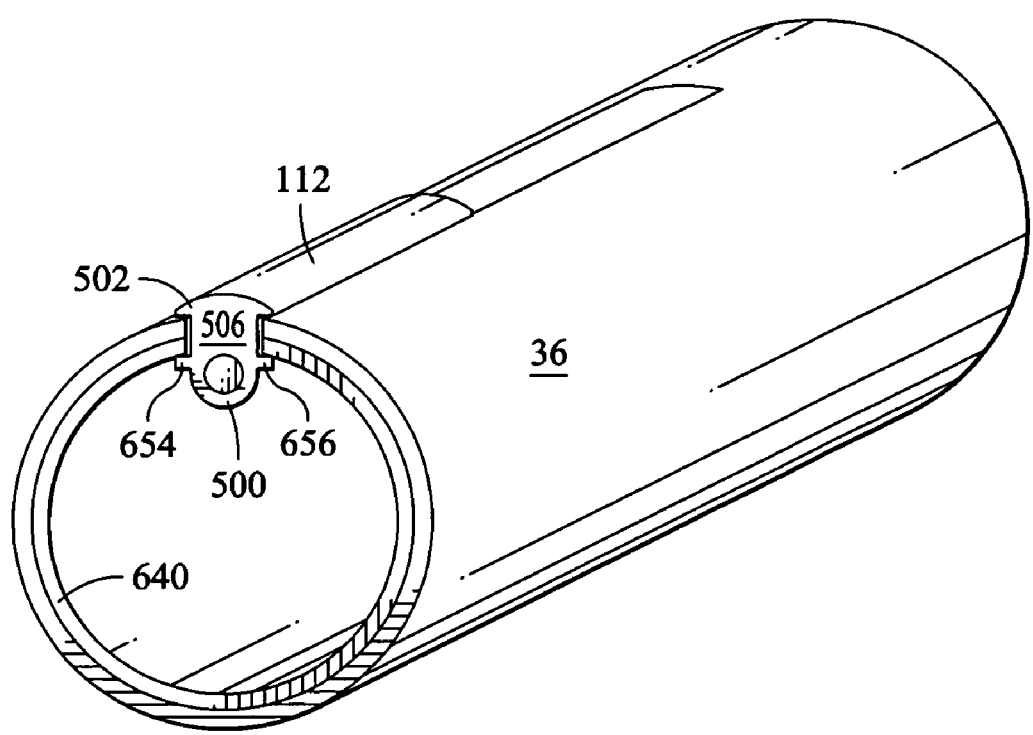
FIG. 27 shows another contact embodiment.

FIG. 27 shows another embodiment for contact 36 and coupling 112. This embodiment presents a "snap lock" design. In this embodiment, conductor coupling 500 has extending edges 654 and 656, which snap into place as coupling 112 is placed within contact slot 508. This embodiment eliminates the need for welding coupling 112 to contact 36 or any other means of added attachment. However, these extra means of attachment could be utilized to ensure a reliable connection. In this embodiment, edges 654 and 656 preferably extend from conductor coupling 500 sufficiently enough to allow coupling 112 to be pushed into contact slot 508 with minimal effort as well as extending far enough to ensure a reliable connection between coupling 112 and contact 36.

Figure 28:
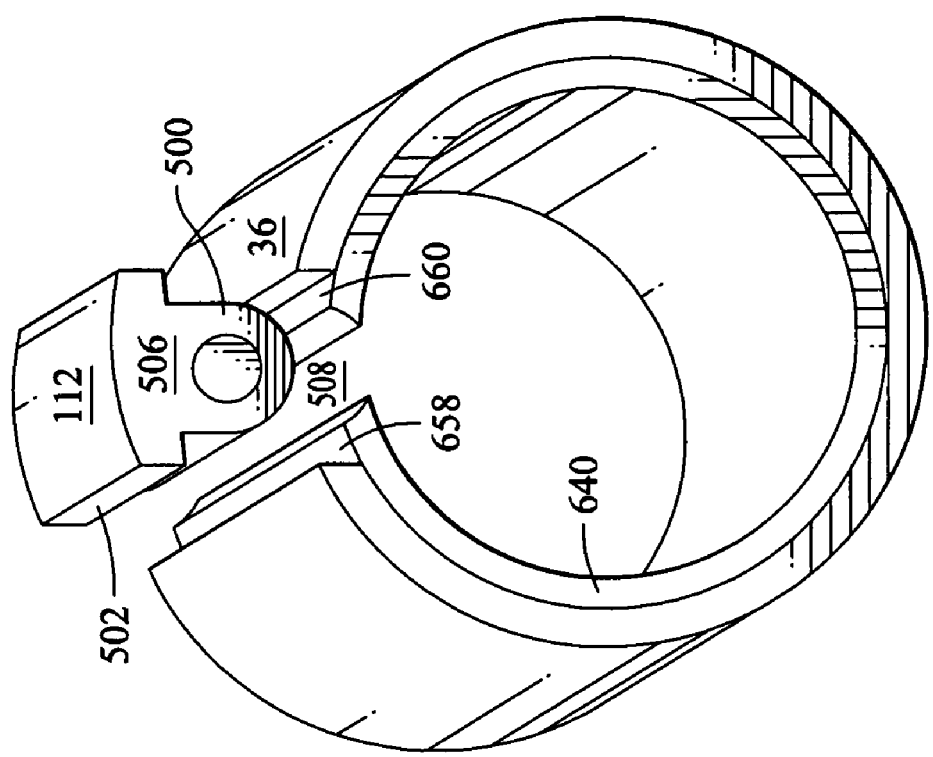
FIG. 28 show another contact embodiment.

FIG. 28 shows another embodiment for contact 36 and coupling 112. This embodiment presents a "T" design. In this embodiment, coupling 112 is in the shape of a capital "T" and rests in contact slot 508 upon ledges 658 and 660. Coupling 112 is then held in place by welding or any other reliable form of attachment.

Figure 29:
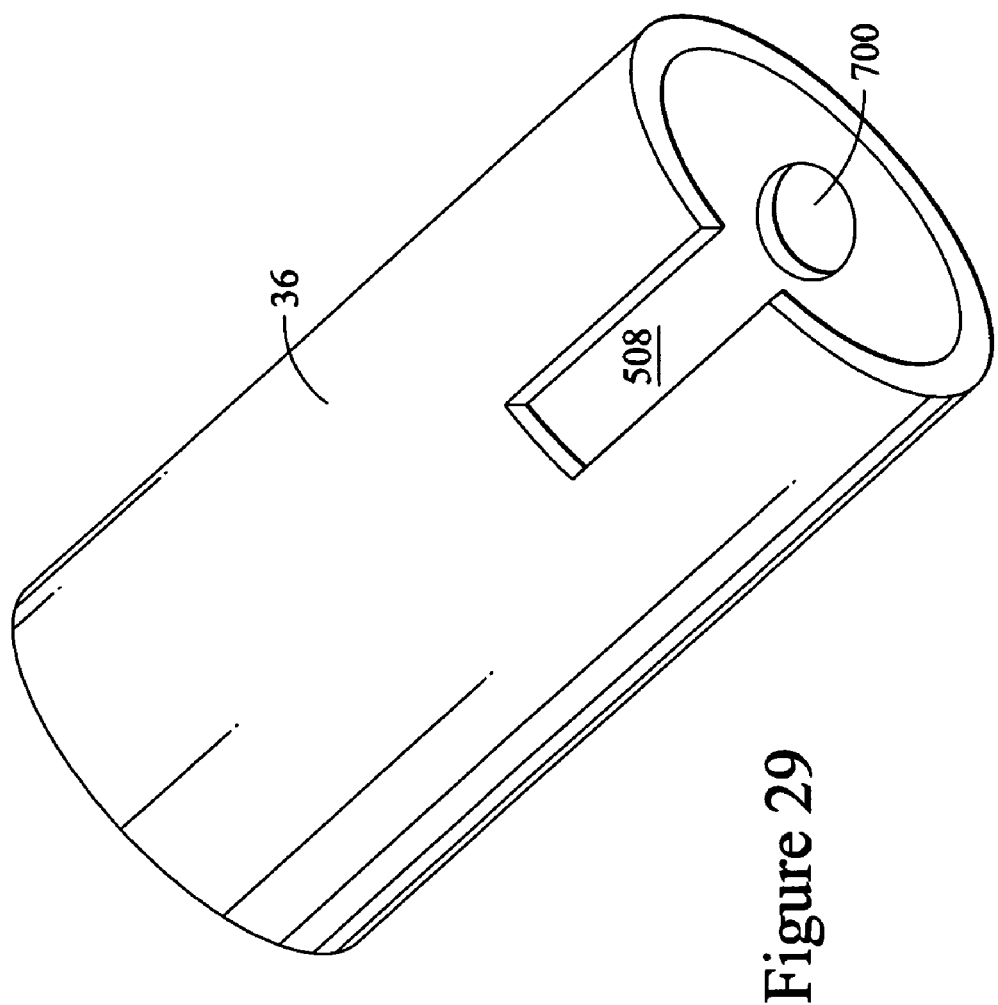
FIG. 29 shows another contact embodiment.

FIG. 29 shows another embodiment for contact 36. This embodiment contains aperture 700 to assist in keeping contact 36 from rotating and keeping it concentric with other contacts 36. When contacts 36 are subjected to an insert molding process where an insulative material is injected between and under the contacts 36, this material fills aperture 700. Then when this insulative material hardens, it locks contact 36 in position and helps prevent contact 36 from rotating and assists in keeping contact 36 concentric with other contacts 36 residing in the same molded section (i.e., the proximal or distal end).

Thus, embodiments of the implantable lead with coplanar contact coupling 502 and method are disclosed to reduce conductor 34 stress. One skilled in the art will appreciate that the present invention can be practiced with embodiments other than those disclosed. The disclosed embodiments are presented for purposes of illustration and not limitation, and the present invention is limited only by the claims that follow.

What is claimed is:

1. A method for performing a coplanar connection between a conductor and a contact on an implantable lead, comprising:
    inserting a conductor into a crimp sleeve cavity of a coupling;
    crimping the crimp sleeve to securely attach the conductor to the crimp sleeve;
    inserting the coupling into a channel formed in the contact;
    positioning the conductor substantially coplanar with the contact body to prevent bending of the conductor; and
    attaching the coupling to the contact.

2. The method of claim 1, wherein the attachment of the coupling to the contact is performed by welding performed substantially on a contact exterior surface for ease of manufacturing.

3. The method of claim 1, wherein the conductor remains within a lead body to reduce communication between patient tissue and the conductor.

4. The method of claim 3, wherein the conductor is retained within a lumen within the lead body.

5. The method of claim 4, wherein the conductor remaining within the lead body reduces ion migration from the conductor outside of the lead body.

6. The method of claim 1, wherein the conductor comprises braided strand wire with a silver core.

7. The method of claim 1, wherein the contact comprises a platinum-iridium alloy.

8. The method of claim 1 wherein the crimp sleeve is comprised of two side arms.

* * * * *